(12) United States Patent
Baek et al.

(10) Patent No.: US 11,492,363 B2
(45) Date of Patent: Nov. 8, 2022

(54) METHOD FOR PREPARATION OF SIZE-MODULATED UIO-66 AND CATALYST FOR HYDROLYSIS OF CHEMICAL WARFARE AGENTS WITH ENHANCED ACTIVITY PREPARED THEREBY

(71) Applicant: KOREA INSTITUTE OF SCIENCE AND TECHNOLOGY, Seoul (KR)

(72) Inventors: Kyung Youl Baek, Seoul (KR); Chong Min Koo, Seoul (KR); Soon Man Hong, Seoul (KR); Seung Sang Hwang, Seoul (KR); Sangho Cho, Seoul (KR); Jin Young Seo, Seoul (KR); Do Xuan Huy, Seoul (KR); Younghan Song, Seoul (KR); Sejin Kim, Seoul (KR); Changju Sung, Seoul (KR); Yeojin Ahn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 474 days.

(21) Appl. No.: 16/395,235

(22) Filed: Apr. 26, 2019

(65) Prior Publication Data

US 2020/0115395 A1 Apr. 16, 2020

(30) Foreign Application Priority Data

Oct. 12, 2018 (KR) .................. 10-2018-0121917

(51) Int. Cl.
| | |
|---|---|
| *B01J 21/06* | (2006.01) |
| *C07F 7/00* | (2006.01) |
| *A62D 3/35* | (2007.01) |
| *A62D 5/00* | (2006.01) |
| *A62D 9/00* | (2006.01) |
| *A62B 18/02* | (2006.01) |
| *B01J 35/10* | (2006.01) |
| *B01J 35/02* | (2006.01) |
| *B01J 31/12* | (2006.01) |
| *A62B 7/10* | (2006.01) |
| *A62D 101/02* | (2007.01) |

(52) U.S. Cl.
CPC ............... *C07F 7/003* (2013.01); *A62B 7/10* (2013.01); *A62B 18/02* (2013.01); *A62D 3/35* (2013.01); *A62D 5/00* (2013.01); *A62D 9/00* (2013.01); *B01J 31/12* (2013.01); *B01J 35/023* (2013.01); *B01J 35/1028* (2013.01); *A62D 2101/02* (2013.01); *B01J 2531/48* (2013.01)

(58) Field of Classification Search
None
See application file for complete search history.

(56) References Cited

U.S. PATENT DOCUMENTS

2016/0175827 A1 6/2016 Hupp et al.

FOREIGN PATENT DOCUMENTS

| CN | 106861627 | * | 1/2017 |
| WO | 2017158165 | * | 9/2017 |

OTHER PUBLICATIONS

Y. Han et al., "Facile synthesis of morphology- and size-controlled zirconium metal-organic framework UiO-66: the role of hydrofluoric acid in crystallization," CrystEngComm, 2015, pp. 6434-6440, vol. 17.
Michael J. Katz et al., "A facile synthesis of UiO-66, UiO-67 and their derivatives," ChemComm, 2013, pp. 9449-9451, vol. 49, The Royal Society of Chemistry.
Korean Office Action for Application No. 10-2018-0121917 dated Oct. 21, 2019. In conformance with MPEP 609—Concise explanation of the relevance includes issue date of KR OA and references cited therein.

* cited by examiner

*Primary Examiner* — Sheng H Davis
(74) *Attorney, Agent, or Firm* — Cantor Colburn LLP

(57) ABSTRACT

The present invention relates to a method for preparing size-modulated UiO-66, which is achieved by modulating the concentrations of reactants, and a catalyst with improved activity of hydrolyzing chemical warfare agents prepared by the method.

11 Claims, 14 Drawing Sheets
(14 of 14 Drawing Sheet(s) Filed in Color)

(A)

(B)

(C)

METHOD FOR PREPARATION OF SIZE-MODULATED UIO-66 AND CATALYST FOR HYDROLYSIS OF CHEMICAL WARFARE AGENTS WITH ENHANCED ACTIVITY PREPARED THEREBY

TECHNICAL FIELD

The present invention relates to a method for preparing size-modulated UiO-66, which is achieved by modulating the concentrations of reactants, and a catalyst with improved activity of hydrolyzing chemical warfare agents prepared by the method.

BACKGROUND ART

Chemical weapons, which are weapons of mass destruction, must be completely eliminated in compliance with the Chemical Weapons Convention (CWC) so that they cannot be used again within the designated period. To fulfill this purpose, it is important to safely and completely eliminate the agents which are the core material of chemical weapons. These agents are toxic chemicals extremely lethal to the human body when people are exposed to even a small amount of these agents in air, and therefore extreme caution is required in their handling.

For this purpose, in handling small quantities of chemical weapons, many countries in the world are using methods in which these agents are separated from ammunition, rockets, mines, etc. and incinerated; or these agents are neutralized with an aqueous alkaline solution, methylethanolamine, etc. and buried or incinerated. In the U.S., with regard to the large-scale treatment of chemical agent stockpiles, as a basic technique, a method is used in which these agents are safely removed from chemical weapons, and the agents and munition bodies are thereafter directly incinerated. However, in the case of direct incineration of chemical warfare agents, they may remain untreated due to incomplete combustion, and additionally, toxic substances may be released to the outside in the form of gases during incineration.

For these reasons, it is necessary to separately install a safety device for preventing the air leakage of these extremely harmful agents during the treatment process, but this safety device has a problem in that it is huge. Additionally, this safety device also has a problem in that when a plurality of activated carbon filters are used to remove harmful gases discharged during incineration, waste activated carbon in which various gases are absorbed must be treated.

Meanwhile, Russia, which possesses the largest amount of chemical weapons in the world, plans to bury its chemical weapons after neutralization and bituminization of the agents. Once these agents are hydrolyzed with water or neutralized with an alkaline substance, the toxicities of these agents are drastically reduced so that the operators can easily handle them without using special equipment. However, the resulting decomposed products still need to be completely converted to non-hazardous materials due to the presence of the CWC-controlled Schedule 2 substances, halogens or acidic substances, and large amounts of salts.

As described above, the treatment of these agents can be carried out by a method of direct incineration or burial of the products generated during hydrolysis. However, in the case of direct incineration of chemical warfare agents, they may remain untreated due to incomplete combustion, and toxic substances may be released to the outside in the form of gases during incineration. Additionally, in a case where the hydrolysate-generating decomposed materials are buried, the decomposed materials may become a major cause of environmental pollution because they contain halogens or acidic substances and a large amount of salts.

Additionally, nerve agents (sarin (or GB), tabun (or GA), and VX) are pyrolyzed at high temperature upon direct incineration, and they commonly produce phosphorus pentoxide ($P_2O_5$), as shown in the following chemical formulas (1) to (3).

When these phosphorus oxides are released into the atmosphere, they cause not only acid rain but also algal blooms.

$$C_4H_{10}FO_2P \text{ (GB (sarin))} + 6\ 1/2\ O_2 \rightarrow 4\ CO_2 + 9/2\ H_2O + HF + 1/2\ P_2O_5$$

$$C_5H_{11}N_2O_2P \text{ (GA (tabun))} + 10\ O_2 \rightarrow 5\ CO_2 + 11/2\ H_2O + 2NO_2 + 1/2\ P_2O_5$$

$$C_{11}H_{26}NO_2PS \text{ (VX)} + 19\ 3/4\ O_2 \rightarrow 11\ CO_2 + 13\ H_2O + 2NO_2 + 1/2\ P_2O_5$$

SUMMARY

With regard to the elimination of toxicities from chemical warfare agents (e.g., organophosphate nerve agents) through a catalytic reaction by UiO-66, the present inventors have made efforts to discover a method for preparing a catalyst which exhibits more improved activity and/or a catalytic hydrolysis method thereof. As a result, they have found that UiO-66 catalysts, in which the size of particles is modulated to be smaller while the size of pores is maintained at a constant level, can be provided by reducing the amount of a solvent used (i.e., reacting by increasing the concentrations of reactants) during the preparation of UiO-66; these size-modulated catalysts can exhibit more improved activity in the hydrolysis reaction of chemical warfare agents and simulants thereof; and in conducting the hydrolysis reaction using these catalysts, a chemical warfare agent is first mixed with a base and finally allowed to come into contact with a catalyst, thus preventing the deterioration of the catalyst by the base and carrying out the reaction with a significantly excellent conversion, thereby completing the present invention.

A first aspect of the present invention provides a method for preparing size-modulated UiO-66, which includes a first step of preparing a first solution comprising $ZrCl_4$ at a concentration of 0.15 M to 0.5 M; a second step of preparing a second solution comprising terephthalic acid (i.e., benzene-1,4-dicarboxylic acid; BDC) at a concentration of 0.1 M to 0.5 M; and a third step of mixing the first solution and the second solution in a ratio of 1:1 to 1:3 to react, in which the first solution comprises hydrochloric acid in an amount of 8 to 15 moles per mole of $ZrCl_4$.

A second aspect of the present invention provides a method for detoxifying chemical warfare agents (CWA) at a conversion rate of at least 50% within one minute, which includes: a first step of adding a solution containing a base and a chemical warfare agent to a water solvent to mix; and a second step of making the solution containing a base and a chemical warfare agent come into contact with UiO-66, which was prepared by the above method.

A third aspect of the present invention provides a protective suit made from fabric, in which the fabric is coated with the UiO-66 prepared by the method of the first aspect.

A fourth aspect of the present invention provides a canister which includes a porous container and the UiO-66 prepared by the above method, which is housed in the container in the form of a molded product.

A fifth aspect of the present invention provides a protective mask including the canister of the fourth aspect.

Hereinafter, the present invention will be described in more detail.

With regard to the preparation of UiO-66 (i.e., a representative catalyst known as having the activity of hydrolyzing chemical warfare agents) and detoxifying the chemical warfare agents through a hydrolysis reaction using UiO-66, the present invention has been designed to discover a method for preparing a catalyst capable of exhibiting more improved activity as a catalyst itself without any additional processes or additives, and conditions for a catalytic reaction using the catalyst.

For these purposes, as a method that can modulate the size and/or defect sites of particles while maintaining the pore size of the particles to be formed, thereby providing particles exhibiting more improved activity, while using a known method, the present inventors have discovered that UiO-66 catalysts with improved activity of catalytic reactions can be provided by proportionally reducing the amount of solvent used while maintaining the ratio of the reactants used (i.e., reacting by increasing their concentrations, thereby reducing the size of the particles and increasing the number of missing linkers within a unit cluster). Furthermore, they have discovered that the hydrolysis reaction can be carried out at a significantly improved conversion rate, by first mixing a chemical warfare agent with a base and then allowing it to come into contact with these UiO-66 catalysts, while performing the hydrolysis reaction of the chemical warfare agent using these UiO-66 catalysts, thereby preventing the deterioration of the catalytic activity by a base used as a reactant, while the hydrolysis reaction of chemical warfare agents is carried out using these UiO-66 catalysts.

To achieve the above objects, an aspect of the present invention provides a method for preparing size-modulated UiO-66, which includes a first step of preparing a first solution containing $ZrCl_4$ at a concentration of 0.15 M to 0.5 M; a second step of preparing a second solution containing terephthalic acid (i.e., benzene-1,4-dicarboxylic acid; BDC) at a concentration of 0.1 M to 0.5 M; and a third step of mixing the first solution and the second solution in a ratio of 1:1 to 1:3 to react, in which the first solution contains hydrochloric acid in an amount of 8 to 15 moles per mole of $ZrCl_4$.

In the method of the present invention, the first step and the second step are arbitrarily named for convenience of explanation and are conducted independently of each other, and the order in which they are conducted does not affect the present invention. For example, the first step and the second step may be conducted sequentially or in reverse order, and may be performed simultaneously.

For example, in the method of the present invention, the first solution and the second solution may be prepared using N,N-dimethylformamide (DMF) as a solvent.

Meanwhile, the third step may be conducted at 60° C. to 120° C. for 12 to 48 hours, but the conditions of the third step are not limited thereto, and the third step may be conducted in consideration of conventional reaction conditions for UiO-66 synthesis.

The UiO-66 particles ultimately prepared according to the preparation method of the present invention may have an average diameter of 50 nm to 400 nm. In particular, the specific surface area and the pore volume of the UiO-66 particles ultimately prepared according to the preparation method of the present invention show relatively constant values with an increase of less than 10%, compared to those of the particles prepared by the conventional method.

The UiO-66 particles synthesized according to the preparation method of the present invention are characterized in that their sizes are reduced as the concentrations of $ZrCl_4$ and terephthalic acid are increased. For example, in a specific embodiment of the present invention, it was confirmed that the UiO-66 particles prepared by reacting a solution, where $ZrCl_4$ (1.62 mmol) was dissolved in DMF (7.5 mL), with a solution, where BDC (2.25 mmol) was dissolved in DMF (7.5 mL), had a size of 590 nm, whereas the UiO-66 particles prepared by reacting these solutions having a 2-fold concentration and a 4-fold concentration by reducing the amount of a solvent for each solution by ½ and by ¼, respectively, had a significantly reduced size of 190 nm and 100 nm, respectively.

Further, the UiO-66 particles ultimately prepared according to the preparation method of the present invention are characterized in that they have an average of 1.65 to 1.9 missing linker sites within a single cluster.

Additionally, these ultimately prepared UiO-66 particles may have a specific surface area of 1,400 $m^2/g$ to 1,500 $m^2/g$. As described above, the UiO-66 particles of the present invention are used by increasing the concentration of the reaction solutions 2-fold and 4-fold compared to the conventional ones, and thus their particle sizes are significantly reduced to 33% and 17%, respectively, whereas their specific surface areas may be maintained at constant levels with an increase of 2% and 5%, respectively.

Another aspect of the present invention provides a method for method for detoxifying chemical warfare agents (CWA) at a conversion rate of at least 50% within one minute, which includes: a first step of adding a solution containing a base and a chemical warfare agent to a water solvent to mix; and a second step of making the solution containing a base and a chemical warfare agent come into contact with UiO-66, which was prepared by the method according to the first aspect.

Examples of the chemical warfare agents (CWA) that can be eliminated using a catalyst may include organophosphate nerve agents (e.g., sarin, soman, cyclosarin, VX, etc.) whose toxicities can be significantly reduced, but the organophosphate nerve agents are not limited thereto.

In particular, the UiO-66 used as a catalyst may be used in an amount of 0.02 to 0.05 moles per 1 mole of CWA. When the amount of the catalyst used is less than 0.02 moles per 1 mole of CWA, a desired degree of reaction cannot be achieved, whereas when the amount of the catalyst used exceeds 0.05 moles, it may result in waste of the excess catalyst.

Since the reaction uses water molecules as a reactant in the hydrolysis reaction, the second step can be carried out in an aqueous solution or in the presence of moisture.

The present invention can provide a protective suit made from fabric which is coated with the UiO-66 prepared according to the present invention.

Additionally, the present invention can provide a canister which receives, in the form of a molded product, a porous container and the UiO-66 prepared according to the present invention within the container. It is preferred that the container has pores at least on one surface thereof so as to allow air to flow in and out. In particular, the molded product is prepared to have predetermined size and shape. The size of the molded product may be 0.3 mm to 5 mm and the shape may be spherical, cylindrical, hexahedral, etc., but the size and shape are not limited thereto. In addition, an air-permeable filtration membrane may be further provided between a molded product of a metal-organic framework the pores of the container, but not limited thereto.

Further, the present invention can provide a protective mask equipped with the canister.

Advantageous Effects of the Invention

The preparation method of the present invention can improve the activity of UiO-66 as a catalyst for the hydrolysis of chemical warfare agents (CWA), by modulating the size of the ultimately synthesized particles by adjusting the concentrations of reactants while using a known preparation method without an additional process or additive. Furthermore, the hydrolysis reaction can be carried out at a significantly increased conversion rate by modulating the reaction conditions with CWA (i.e., sequence), and thus can be effectively used for the preparation of protective clothing or protective masks.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
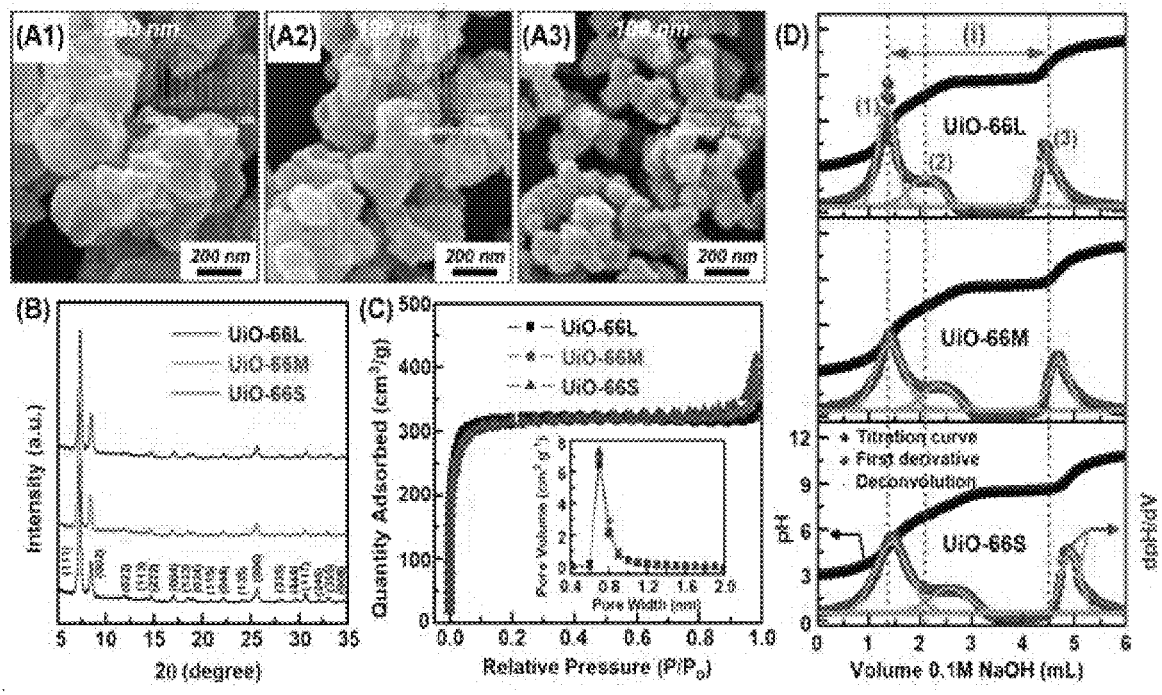
FIG. 1 shows representative SEM images of modulated UiO-66 with different sizes, ((A1): large-size (UiO-66L), (A2): medium-size (UiO-66M), and (A3): and small-size (UiO-66S)) (inset: particle size distribution derived from SEM images with Langmuir of a solid red solid line); (B) PXRD patterns of UiO-66L, UiO-66M, and UiO-66S; (C) N2 adsorption/desorption isotherms curves with a pore size distribution of UiO-66L, UiO-66M, and UiO-66S; and (D) acid-base titration curves with first derivatives and its deconvolution plots using mixed Gaussian-Lorentzian functions.

Hereinafter, the present invention will be described in more detail through Examples. However, these Examples are intended to further illustrate the present invention, and the scope of the present invention is not limited by these Examples.
<Materials>

All of the reagents, including zirconium(IV) chloride (ZrCl$_4$, ≥99.5%), hydrochloric acid (HCl, 36.5% to 38.0%), benzene-1,4-dicarboxylic acid (BDC, 98%), dimethylformamide (DMF, 99.8%), 4-ethylmorpholine (4-EM, 97%), linear-type polyethyleneimine (LPEI, M$_n$=10 k), and branch-type polyethyleneimine (BPEI, M$_n$=0.6 k and 10 k) were purchased from Sigma-Aldrich and were used as received unless otherwise noted. Methylparaoxon (MPO, Sigma-Aldrich) was used after dilution in methanol (0.253 mmol/mL).

Example 1

Synthesis of Size-Modulated UiO-66 Catalysts

The size-modulated UiO-66 catalysts were synthesized by the following method. Specifically, two solutions were prepared separately such that one solution contained ZrCl$_4$ (1.62 mmol, 0.38 g), one-third of the DMF, and HCl (1.5 mL) and the other solution contained BDC (2.25 mmol, 0.37 g) and the remaining DMF, and these two solutions were stirred at 50° C. until they were well dissolved. In particular, for the size modulation of UiO-66 catalysts (e.g., for the preparation of UiO-66 catalysts in sequential order of size), the total DMF volume was changed to 45 mL for UiO-66L (large size), 22.5 mL for UiO-66M (medium size), and 11.25 mL for UiO-66S (small size). The former solution (i.e., the ZrCl$_4$-containing solution) was poured into the latter solution, heated at 80° C., and then retained thereat for 24 hours to allow a reaction to occur between them. After dilution with DMF of the same volume used for the reaction, the precipitates were filtered and continuously washed with an excess of DMF and ethanol. The obtained UiO-66 catalysts were dried at 90° C. overnight and activated by drying at 150° C. for 3 hours before using them as a catalyst. A scale-up process for UiO-66S was performed with a 200-times larger scale, and the process was performed the same as described for the synthesis of UiO-66S.

Example 2

Catalytic Activity for Hydrolysis of MPO by Size-Modulated UiO-66

The catalytic activity of the hydrolysis reaction of methylparaoxon (MPO) by UiO-66, prepared in Example 1, was monitored using $^{31}$P NMR.

A 5 mL vial with a 0.58 mL H$_2$O/D$_2$O (9/1) mixture was prepared and 4-EM (0.45 mmol) and 0.1 mL of diluted MPO in methanol (0.253 mmol/mL) were sequentially added thereto.

(1) Method 1: A 5 mL vial with a 0.58 mL H$_2$O/D$_2$O (9/1) mixture was prepared, and 4-EM (0.45 mmol) and 0.1 mL MPO diluted in methanol (0.253 mmol/mL) were sequentially added thereto. The mixture was stirred for 30 seconds, and after one minute, 0.32 mL of a UiO-66 suspension in water was finally added to the above solution prepared in advance. After a predetermined time, a sample of 20 μL was taken and diluted with 0.7 mL of D$_2$O. Then, the diluted solution was filtered to remove the UiO-66 catalysts. The obtained solution was used for evaluation of the hydrolysis rate by $^{31}$P NMR.

(2) Method 2: A 5 mL vial with a 0.58 mL H$_2$O/D$_2$O (9/1) mixture was prepared, and 4-EM (0.45 mmol) and 0.32 mL of a UiO-66 suspension in water (5 mg/mL) were sequentially added thereto. After stirring the mixture for one day, 0.1 mL of MPO diluted in methanol (0.253 mmol/mL) was finally added to the above solution prepared in advance. Evaluation of the hydrolysis rate was performed by following the method used in Method 1.

(3) Method 3: A 5 mL vial with a 0.58 mL H$_2$O/D$_2$O (9/1) mixture was prepared, and 4-EM (0.45 mmol) and 0.32 mL of a UiO-66 suspension in water (5 mg/mL) were sequentially added thereto. The mixture was stirred for 30 seconds, and after one minute, 0.1 mL of MPO diluted in methanol (0.253 mmol/mL) was finally added to the above solution prepared in advance.

In the case of the reactions with BPEI, an in situ reaction method, in which the prepared reaction solution according to Method 1 or Method 2 was transferred to an NMR tube, was performed, and the $^{31}$P NMR spectra were immediately measured without further sampling.

Example 3

Computational Details

To investigate chemical reactions between UiO-66 structures and small agents, density functional theory (DFT)

calculations were carried out within the framework of M06-L Meta-Generalized Gradient Approximation. In particular, for non-metal atoms, the def2-SVP basis set was used, whereas, for Zr, SRSC pseudo-potential was considered to effectively describe the outer valence region. All total energies for optimized structures were corrected by considering the zero point energy, and free energy change for the chemical reactions between UiO-66 and agents was computed at 298 K, which was obtained through frequency calculations. The DFT calculations were performed with the Q-Chem 5.0 modeling suite. To represent the UiO-66 MOF structure, a cluster model (e.g., a local framework of UiO-66 consisting of 6 Zr atoms, 8 oxygen atoms and 12 bridging ligands) was used so the total number of atoms for the unit structure of UiO-66 became 186. This number was too large to calculate for the present calculation level where the benzene rings of the 12 ligands are omitted to focus on the interaction on the metal sites and terminated with hydrogen atoms. For the description of defects, one carboxylate ligand (COOH) was omitted and two Zr atoms were exposed to water molecules or agents. One Zr site was assumed to be occupied by hydroxyl groups for all geometries, which is reasonable due to its high binding energy, as will be shown later.

Example 4

Characterizations

Powder X-ray diffraction (XRD) patterns were obtained on a Rigaku diffractometer (Rigaku Smart Lab, Rigaku Co., Japan) operated at 45 kV and 40 mA with CuKα radiation ($\lambda$=1.5406 Å) using a diffracted beam monochromator. Data were collected between 2θ=5° and 2θ=35° at 0.01° intervals. X-ray photoelectron spectroscopy (XPS) analysis was performed under reduced pressure using an X-ray photoelectron spectrometer (X-TOOL, ULVAC-PHI) with a monochromatic AlKα source. Potentiometric titrations were performed with a Titrando 905 (Metrohm) equipped with Dosino 800 (Metrohm). Thermal analysis was performed by thermogravimetric analysis (TGA, TA instruments TGA 2950) at a heating rate of 10° C./min under a $N_2$ atmosphere. $^1$H NMR and $^{31}$P NMR spectra were recorded using a mixed solvent of $H_2O/D_2O$=9/1 (v/v) at 25° C. on a Varian Unity INOVA (300 MHz). Fourier transform infrared (FT-IR) spectra were measured by Thermo Scientific Nicolet FT-IR system (iS10) using a solvent casting method on KBr pellets. The morphological analysis was performed by the scanning electron microscope (SEM) Inspect F50. $N_2$ adsorption-desorption isotherms and pore size distribution were measured at 77 K using a Brunauer-Emmett-Teller (BET) instrument (ASAP 2010, Micromeritics). Before BET measurement, all of the samples were degassed overnight at 200° C. under reduced pressure.

<Results>

UiO-66 materials with modulation were synthesized using a DMF solution containing $ZrCl_4$, BDC, and HCl (1.5 mL) by the method according to Example 1. In brief, two separate solutions containing $ZrCl_4$/HCl and BDC in DMF, respectively, were mixed by pouring the $ZrCl_4$/HCl solution into the BDC solution and then heated at 80° C. for 24 hours. To modulate the size of UiO-66 particles, only the DMF solvent volume was changed within a range of 45 mL to 11.2 mL, and the total amounts of reactants used as modulation parameters are shown in Table 1. The resulting products prepared at three different reaction concentrations were examined with regard to their morphology and size by SEM. As a result, the three resulting UiO-66 materials were shown to have sizes of 580 nm, 190 nm, and 100 nm, in the order of the highest amount of DMF (total amount of DMF in a range of 45 mL to 11.2 mL) used as a solvent (i.e., in the order of the increasing concentration of the reactants), and they were expressed hereinafter as UiO-66L, UiO-66M, and UiO-66S according to their particle size, respectively (FIG. 1A). The SEM image of the UiO-66L showed a non-spherical shape along with broad size distribution (FIG. 1(A1)). In contrast, the UiO-66S exhibited a shape which is mostly spherical with relatively narrow size distribution (FIG. 1(A3)). The modulated size of UiO-66 by varying the reaction concentration can be explained by the roles of HCl during the framework, which delays the hydrolysis of $ZrCl_4$ as well as the deprotonation of BDC. In particular, the increase of the reaction concentration can further facilitate the neutralization of charges of Zr cations by abundant Cl anions. In UiO-66 synthesis, the reaction concentration-dependent changes in size were confirmed using hydrofluoric acid (HF) as a modulator by Han et al. (*CrystEngComm.*, 2015, 17: 6434 to 6440). The present inventors had previously synthesized UiO-66 by varying their size, which agreed with the results of the present invention. However, unlike the present invention, as the amount of hydrofluoric acid used increased or the concentration of the reactants increased, the size of the particles being formed was significantly increased while the size of the pores was maintained at the same level. In contrast, in the present invention, where hydrochloric acid is used as a modulator, as the amount of the solvent used decreased (i.e., with the increase of the concentration of reactants), the size of the particles being formed was shown to decrease. This phenomenon was similarly applied in the case of mass production of increasing the reaction volume by 100 times (see Tables 1 and 2).

TABLE 1

| Sample | BDC (mmol) | $ZrCl_4$ (mmol) | HCl (mL) | DMF (mL) |
|---|---|---|---|---|
| UiO-66L | 2.25 | 1.62 | 1.5 | 45.0 |
| UiO-66M | 2.25 | 1.62 | 1.5 | 22.5 |
| UiO-66S | 2.25 | 1.62 | 1.5 | 11.2 |
| UiO-66S (Scale-up) | 450 | 324 | 300 | 2200 |
| UiO-66$_{HCl}$ | 0.75 | 0.54 | 1.0 | 15.0 |

TABLE 2

| | BET | | | Titration | | |
|---|---|---|---|---|---|---|
| Sample | Surface Area ($m^2/g$) | Pore Volume ($cm^3/g$) | Missing Linkers per Unit Cluster | $H^+$ Content$^a$ calculated from Defects (mmol) | Content$^b$ of Consumed $OH^-$ (mmol) | Size $D_{SEM}{}^c$ |
| UiO-66L | 1394 | 0.50 | 1.6 | 0.317 | 0.317 | 580 |
| UiO-66M | 1424 | 0.51 | 1.7 | 0.339 | 0.337 | 190 |

TABLE 2-continued

| | BET | | | Titration | | |
| --- | --- | --- | --- | --- | --- | --- |
| Sample | Surface Area ($m^2/g$) | Pore Volume ($cm^3/g$) | Missing Linkers per Unit Cluster | $H^+$ Content[a] calculated from Defects (mmol) | Content[b] of Consumed $OH^-$ (mmol) | Size $D_{SEM}$[c] |
| UiO-66S | 1463 | 0.54 | 1.8 | 0.361 | 0.360 | 100 |
| UiO-66S (Scale-up) | 1459 | 0.54 | — | — | — | 100 |
| UiO-66$_{HCl}$[1,2] | 1580 | NA | 1.6 | 0.313[d] | 0.311[d] | 400 |

[a]The values were estimated from the formula with a specific number of missing linkers (see Table 3).
[b]The consumed $OH^-$ content was calculated using the NaOH titrant consumed between equivalence points of (1) and (3) in FIG. 1D.
[c]$D_{SEM}$ was determined by SEM images.
[d]The values were obtained using samples (0.049 g) and others were obtained using catalysts (0.05 g) for titration.
[1]Katz, M. J. et al., A facile synthesis of UiO-66, UiO-67 and their derivatives, *Chem. Commun.*, 2013, 49: 9449 to 9451.
[2]Katz, M. J. et al., Simple and compelling biomimetic metal-organic framework catalyst for the degradation of nerve agent simulants, *Angew. Chemie - Int. Ed.*, 2014, 53: 497 to 501.

TABLE 3

| Missing Linker | Molecular Formula | MW | Amount of $H^+$ (mmol) from Defects in Sample (0.050 g) | Amount[a] of $OH^-$ Consumed between (1) and (3) (mmol) | Matched Samples |
| --- | --- | --- | --- | --- | --- |
| 1 | $Zr_6O_4(OH)_4(C_8H_4O_4)_5[(H_2O)(OH)]_2$ | 1,570.0 | 0.191 | | |
| 1.1 | $Zr_6O_4(OH)_4(C_8H_4O_4)_{4.9}[(H_2O)(OH)]_{2.2}$ | 1,560.6 | 0.211 | | |
| 1.2 | $Zr_6O_4(OH)_4(C_8H_4O_4)_{4.8}[(H_2O)(OH)]_{2.4}$ | 1,551.1 | 0.232 | | |
| 1.3 | $Zr_6O_4(OH)_4(C_8H_4O_4)_{4.7}[(H_2O)(OH)]_{2.6}$ | 1,541.7 | 0.253 | | |
| 1.4 | $Zr_6O_4(OH)_4(C_8H_4O_4)_{4.6}[(H_2O)(OH)]_{2.8}$ | 1,532.3 | 0.274 | | |
| 1.5 | $Zr_6O_4(OH)_4(C_8H_4O_4)_{4.5}[(H_2O)(OH)]_3$ | 1,522.9 | 0.295 | | |
| 1.55 | $Zr_6O_4(OH)_4(C_8H_4O_4)_{4.45}[(H_2O)(OH)]_{3.09}$ | 1,517.9 | 0.305 | | |
| 1.6 | $Zr_6O_4(OH)_4(C_8H_4O_4)_{4.4}[(H_2O)(OH)]_{3.2}$ | 1,513.5 | 0.317 | 0.317 | UiO-66L |
| 1.7 | $Zr_6O_4(OH)_4(C_8H_4O_4)_{4.3}[(H_2O)(OH)]_{3.4}$ | 1,504.1 | 0.339 | 0.337 | UiO-66M |
| 1.8 | $Zr_6O_4(OH)_4(C_8H_4O_4)_{4.2}[(H_2O)(OH)]_{3.6}$ | 1,494.7 | 0.361 | 0.360 | UiO-66S |
| 2 | $Zr_6O_4(OH)_4(C_8H_4O_4)_4[(H_2O)(OH)]_4$ | 1,475.9 | 0.407 | | |

[a]The values were derived from the mean values of three trials in Table 4 below The PXRD patterns of a series of UiO-66 exhibited that the synthesized materials have the isostructure with UiO-66 in addition to suggesting their high crystallinity (FIG. 1B). FIG. 1C displays the $N_2$ adsorption-desorption isotherms for UiO-66L, UiO-66M, and UiO-66S, exhibiting the surface area of 1,394 $m^2 g^{-1}$, 1,424 $m^2 g^{-1}$, and 1,463 $m^2 g^{-1}$, respectively. Although the surface area for all of the UiO-66 materials showed similarity, it can be seen that UiO-66S with a smaller size exhibited the highest surface area and sequentially followed by UiO-66M and UiO-66L. The particle-size-dependent changes in the surface area were shown, in which the surface area increased according to a decrease in particle size (Table 2). The pore size distribution of all of UiO-66 showed mostly similar curve shapes, and the peak points were centered at 0.7 nm (FIG. 1C inset). However, the pore volume slightly increased with a decrease of particle size, which was a result contrary to what was normally expected, because the pore volume should be the same based on the structure perfection of UiO-66. Meanwhile, the changes by defect sites in UiO-66 suggest that the changes in the reaction concentration can induce tuning of the missing linker density and surface area in the prototypical UiO-66. Furthermore, an increase of missing linkers in UiO-66 enables a high hydrolysis rate by accessible and available Lewis acidic Zr moieties.

Figure 2:
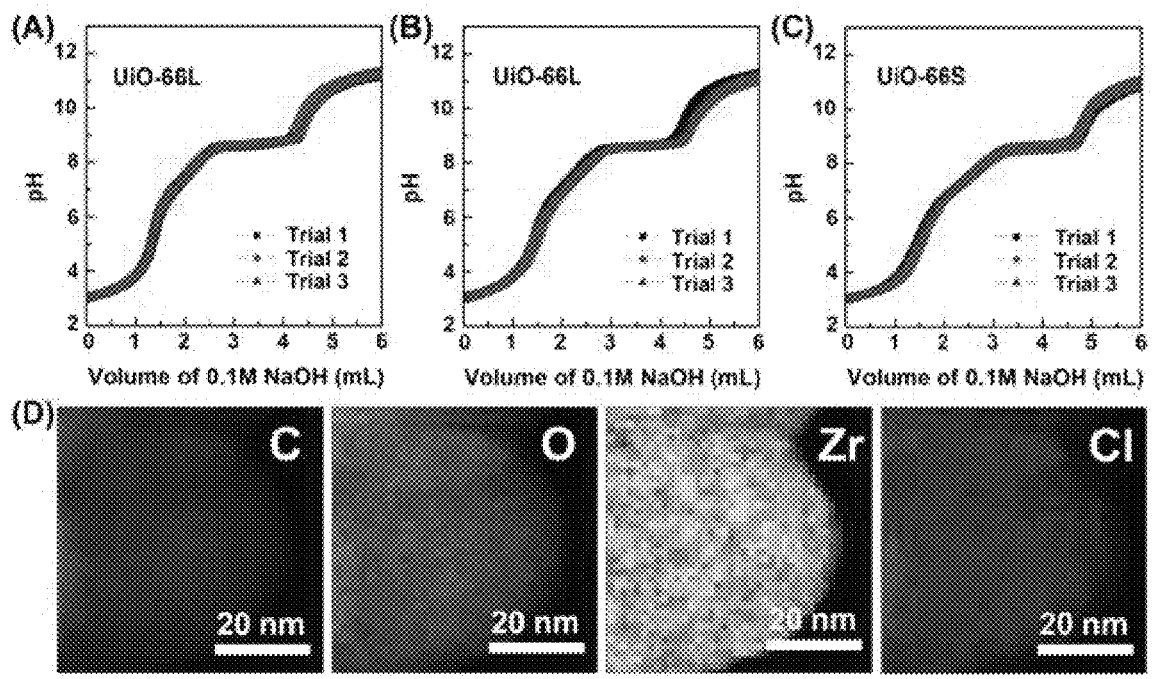
FIG. 2 shows the overlay of three acid-base titration curves for (A) UiO-66L, (B) UiO-66M, and (C) UiO-66S; and (D) the results of element mapping of STEM-EELS of UiO-66S.
Figure 3:
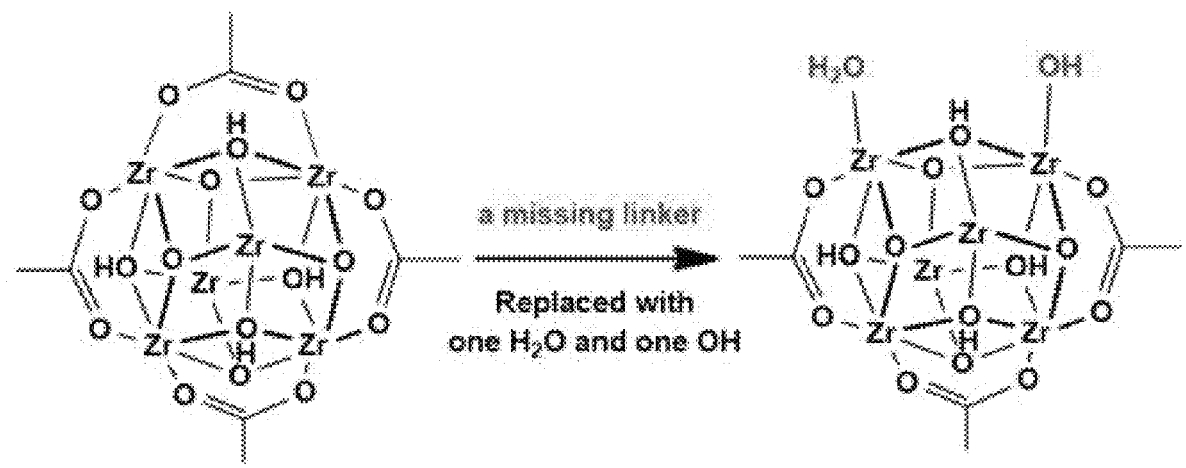
FIG. 3 shows a schematic diagram illustrating defect sites in a UiO-66 cluster derived from a missing linker (the chemical structures of BDC linkers are omitted for clarity purpose of the cluster).

With regard to the tunable defect sites on the UiO-66 structure, the present inventors have quantitatively analyzed the number of missing linker numbers per cluster using a potentiometric titration method. The potentiometric titration was performed according to the Klet method (*J. Mater. Chem. A*, 2016, 4: 1479 to 1485; *ACS Catal.*, 2015, 5: 4637 to 4642). Specifically, the titration was tested using the UiO-66 dispersed in an aqueous $NaNO_3$ solution, and then the pH of the solution was adjusted to pH 3 using concentrated HCl. Acid-base titration with synthesized UiO-66 catalysts was performed by dropwise addition of the 0.1 M NaOH aqueous solution into the prepared UiO-66 solution until its pH reached 10.5, and the pH changes were measured (FIGS. 1D and 2). All of the UiO-66 samples were tested 3 times, and the mean values were used to calculate the number of their missing linkers (FIG. 2). This method has been considered as an improved method for quantifying the missing linkers compared to the approach using thermogravimetric analysis (TGA) even though the defect sites have not been precisely identified, but the missing linkers can be replaced with $-OH_2$ and $-OH$ from the aspect of charge neutralization (FIG. 3). It should be noted that the charge compensation resulting from missing linkers can depend on its synthetic protocol and types of modulators. In addition, some estimates based on Klet's report should be discussed as follows: (1) the missing linkers range as high as two per UiO-66 cluster and (2) the protons provided from defect sites should be probed during titration. In FIG. 1D, all of the UiO-66 titration curves present the typical three equivalence points assigned with (1), (2), and (3), which correspond to (1) $\mu_3$-OH, (2) $-H_2O$, and (3) $-OH$, respectively. The assignment indicated that the titratable protons at (2) and (3) equivalence points can be derived from defect sites. The number of missing linkers was calculated using the consumed NaOH titrant between the first equivalence point (1) and last equivalence (3) point, and are shown in FIG. 1D. The more extensive consumption of NaOH for the third equivalence indicates that a more massive content of protons is needed for titration, in addition to a larger number of missing linkers presented (FIG. 1D and Table 2). Based on the suggested method from Klet's report, the number of missing linkers per cluster was evaluated to be 1.6, 1.7, and 1.9, which corresponded to UiO-66L, UiO-66M, and UiO-66S, respectively (Table 2). The resulting values are considered to be reasonable compared to the reported values including Klet's report (UiO-66$_{HCl}$: 1.6) (Tables 2 and 4). The increase of missing linkers according to an increase of reaction concentration was thought to be due to the effect of the delayed $ZrCl_4$ hydrolysis, which induces the remaining Zr—Cl coordination in the final products. To confirm this experimentally, STEM-EELS element mapping was performed and the results are shown in FIG. 2 (D). As shown in FIG. 2 (D), in the UiO-66S just synthesized, the chlorine element was uniformly dispersed throughout the particles, and the content thereof was 4.2 atomic % (at %). As such, the number of the estimated missing linkers derived for UiO-66L, UiO-66M, and UiO-66S demonstrated that the changes in the reaction concentration enable the changes in the defect site densities as well as the size in the UiO-66 synthesized by HCl as a modulator.

TABLE 4

| Sample | | Amount[a] of OH⁻ Consumed between (1) and (3) (mmol) | Mean Value |
|---|---|---|---|
| UiO-66L | Trial 1 | 0.32 | 0.317 |
| | Trial 2 | 0.33 | |
| | Trial 3 | 0.30 | |
| UiO-66M | Trial 1 | 0.34 | 0.337 |
| | Trial 2 | 0.35 | |
| | Trial 3 | 0.32 | |
| UiO-66S | Trial 1 | 0.37 | 0.360 |
| | Trial 2 | 0.36 | |
| | Trial 3 | 0.35 | |

[a]The values were calculated using (i) in FIG. 1D, and the actual acid-base titration curves obtained by 3 trials are shown in FIG. 2. These trials exhibited reproducibility.

Figure 4:
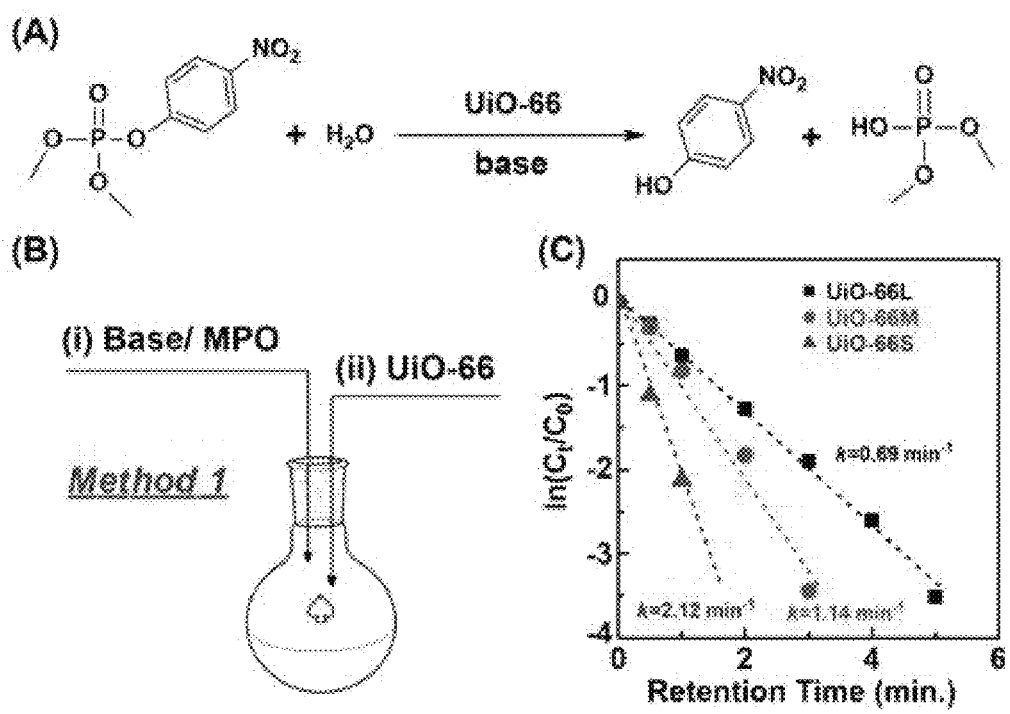
FIG. 4 shows (A) a hydrolysis process of methylparaoxon (MPO) by UiO-66 in the presence of a base; (B) a catalytic reaction process, which is suggested as Method 1 in which (i) a base/MPO mixture is prepared; and (ii) UiO-66 is finally added to the mixture (the present invention is fulfilled through this process unless otherwise specified); and (C) the results of the $\ln(C_t/C_0)$ vs. t plot for hydrolysis of MPO in the presence of UiO-66L, UiO-66M, and UiO-66S catalysts (0.95 μmol each), along with 4-EM (450 mM).
Figure 5:
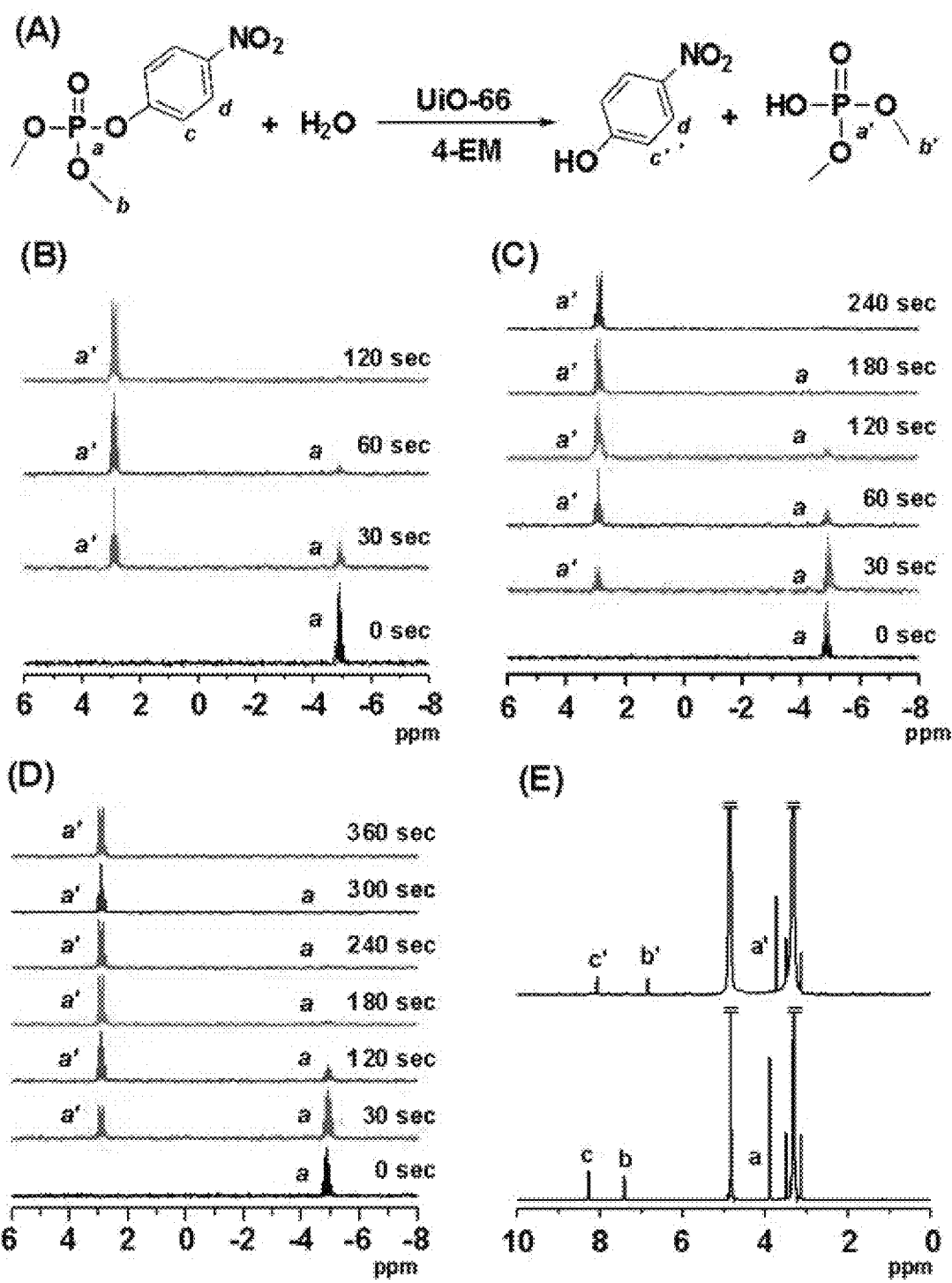
FIG. 5 shows (A) a hydrolysis of MPO using UiO-66 in the presence of 4-EM; $^{31}$P NMR spectra for hydrolysis of MPO by (B) UiO-66S; (C) UiO-66M; and (D) UiO-66L measured in $H_2O/D_2O=9/1$ (v/v) after filtration to remove the catalyst at the predetermined time; and (E) NMR spectra of MPO (bottom) and hydrolyzed resultants thereof including p-nitrophenol and dimethoxy phosphate (top) measured in $H_2O/D_2O=9/1$ (v/v).

Evaluation of catalytic activity for synthesized UiO-66 catalysts was performed by a model reaction using hydrolysis of MPO, which is a nerve agent simulant (FIG. 4A). The chemical structure of the MPO simulant has high similarity to those of actual nerve agents, and its catalytic activity is known to be relatively low compared to that of actual nerve agents. Furthermore, the toxicity is significantly lower than that of actual nerve agents. Therefore, the MPO has been used as an effective nerve agent simulant to examine the newly developed catalysts for detoxification of nerve agents. According to those known in the art, MPO can be hydrolyzed into p-nitrophenol and dimethoxy phosphate by Zr(IV)-based MOFs in the presence of a base including 4-EM and PEI, as shown FIG. 4A. The hydrolysis reactions of MPO by synthesized UiO-66 catalysts were performed as follows by the Method 1 in FIG. 4B, specifically the method in which the UiO-66 suspension in water was added into the prepared aqueous solution of 4-EM and MPO after one minute. The hydrolysis rates of synthesized UiO-66 catalysts in the catalyzed reaction with MPO were measured by $^{31}$P NMR after quantifying the concentrations of MPO (α) and dimethoxy phosphate (α') (FIGS. 5B to 5D). Additionally, the chemical structures of p-nitrophenol and dimethoxy phosphate were confirmed by $^1$H NMR after hydrolysis of MPO, and the results are shown in FIG. 5E with structure assignments. The $^{31}$P NMR spectra for hydrolysis of MPO by UiO-66S showed a significant decrease of the MPO peak at −4.9 ppm and an increase of the dimethoxy phosphate peak at 2.9 ppm with an increase of the reaction time, indicating the relatively fast kinetics in the hydrolysis of MPO compared to that by UiO-66M and UiO-66L (FIG. 5B). For more accurate evaluation of the catalytic hydrolysis rate of UiO-66, the reaction rate constant was determined using the pseudo-first order reaction kinetics, which can be normalized and described by the following Equation 1:

$$ln(C_t/C_0) = -kt \quad (1)$$

where $C_t$ is the concentration of MPO at time t, $C_0$ is the initial concentration of MPO, and k is the pseudo-first-order rate constant. The $ln(C_t/C_0)$ vs. t plot for the hydrolysis of MPO catalyzed by UiO-66L, UiO-66M, and UiO-66S (0.95 μmol each) showed a linear relationship between $ln(Ct/C_0)$ and t, which corresponded to the pseudo-first order reaction kinetics (FIG. 4C).

In addition, UiO-66S showed a substantially higher rate constant (2.12 min$^{-1}$), sequentially followed by UiO-66M (1.145 min$^{-1}$) and UiO-66L (0.688 min$^{-1}$) (Table 5, entries 1-3). However, the pseudo-first-order rate constant (k) did not explain the intrinsic catalytic activity of catalysts because the value did not include the information with regard to the number of reactive sites in the catalyst. The comparative evaluation of the synthesized UiO-66 catalysts in the intrinsic catalytic activity was performed by calculation of the turnover frequency (TOF), which can be defined by the following Equation 2:

$$TOF = \frac{M_{sub} \times X}{M_{cat} \times t} \quad (2)$$

where $M_{sub}$ and $M_{cat}$ are the amounts of a substrate and a catalyst, respectively; X is the conversion of a substrate, t is the reaction time. The TOF values of the synthesized UiO-66 catalysts are shown in Table 5. As a result, it was found that UiO-66S showed higher catalytic activity (0.548 sec$^{-1}$) compared to UiO-66M (0.239 sec$^{-1}$) and UiO-66L (0.188 sec$^{-1}$). The TOF value of UiO-66S was shown to be 3 times higher than that of UiO-66L.

TABLE 5

| Order | Method | Catalyst[a] | Amount of Catalyst (μmol) | Base | Base Conc. (mM) | k[b] (min$^{-1}$) | TOF[c] (sec$^{-1}$) | $t_{1/2}$ (min) |
|---|---|---|---|---|---|---|---|---|
| 1 | 1 | UiO-66L | 0.95 | 4-EM | 450 | 0.688 | 0.188 | 1.0 |
| 2 | 1 | UiO-66M | 0.95 | 4-EM | 450 | 1.145 | 0.239 | 0.6 |
| 3 | 1 | UiO-66S | 0.95 | 4-EM | 450 | 2.121 | 0.548 | 0.3 |
| 4 | 1 | UiO-66S | 0.71 | 4-EM | 450 | 1.342 | 0.235 | 0.5 |
| 5 | 1 | UiO-66S | 0.44 | 4-EM | 450 | 0.004 | 0.014[d] | >40 |

TABLE 5-continued

| Order | Method | Catalyst[a] | Amount of Catalyst (μmol) | Base | Base Conc. (mM) | $k^b$ (min$^{-1}$) | TOF$^c$ (sec$^{-1}$) | $t_{1/2}$ (min) |
|---|---|---|---|---|---|---|---|---|
| 6 | 1 | UiO-66S | 0.95 | LPEI10k | 0.9 (9 mg) | 0.255 | 0.219 | 2.7 |
| 7 | 1 | UiO-66S | 0.95 | BPEI10k | 0.9 (9 mg) | 0.047 | 0.018 | 14.7 |
| 8 | 1 | UiO-66S | 0.95 | BPEI0.6k | 15 (9 mg) | 0.007 | 0.007$^d$ | >60 |
| 9 | 2 | UiO-66S | 0.95 | LPEI10k | 0.9 (9 mg) | 0.001 | 0.001$^d$ | >60 |
| 10 | 2 | UiO-66S | 0.95 | 4-EM | 450 | 0.003 | 0.003$^d$ | >60 |
| 11 | 3 | UiO-66S | 0.95 | 4-EM | 450 | 0.006 | 0.005$^d$ | >60 |
| 12 | 4$^e$ | UiO-66 | 1.5 | 4-EM | 450 | — | 0.004 | 35$^3$ |
| 13 | 4$^e$ | UiO-66-NH$_2$ | 1.5 | 4-EM | 450 | — | 0.140 | 1.0$^4$ |
| 14 | 4$^e$ | NU-1000 | 1.5 | 4-EM | 390 | — | 0.017 | 8.3$^5$ |
| 15 | 4$^e$ | NU-1000 | 1.5 | LPEI$^f$ | 3 (7.5 mg) | — | 0.017 | 8.4$^5$ |

Figure 13:
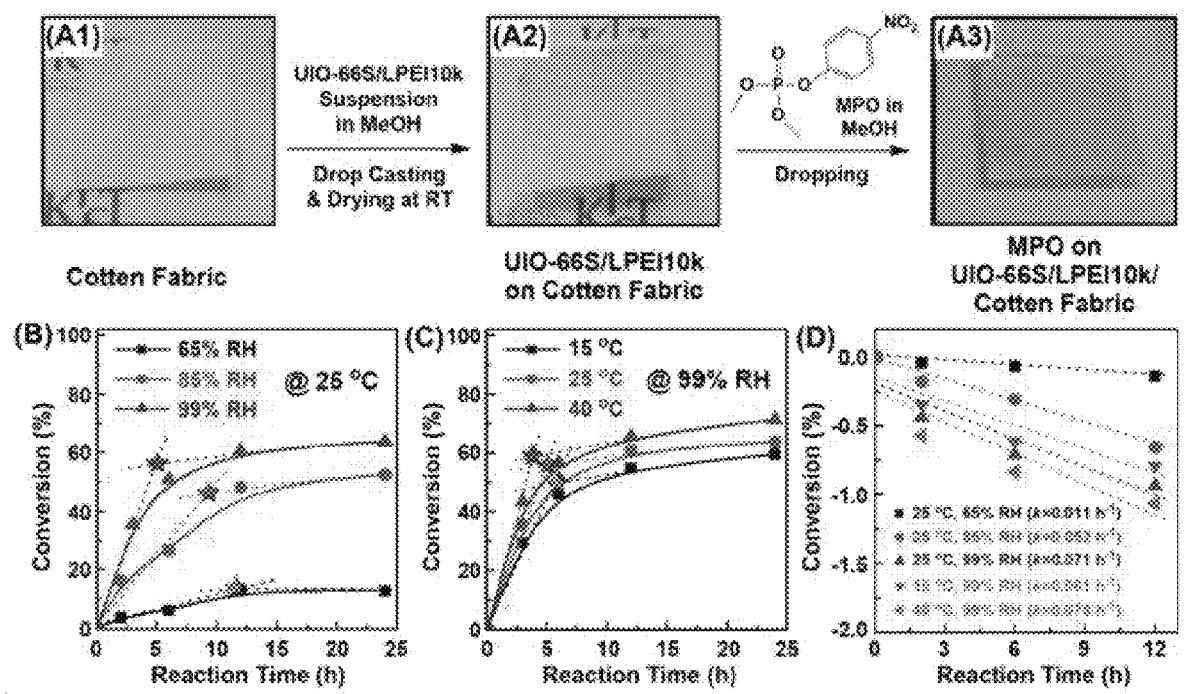
FIG. 13 shows the representative images for a controlled hydrolysis reaction of MPO as a function of either humidity or temperature, in which (A1) represents 1×1 cm$^2$-sized cotton fabric, (A2) UiO-66S/LPEI10k composite-coated cotton fabric prepared by drop-casting with methanol suspension of UiO-66S/LPEI10k and then dried at RT, (A3) presence of MPO diluted in methanol onto the UiO-66S/LPEI10k composite-coated cotton fabric; (B) hydrolysis profiles of MPO by UiO-66S with different humidity at 25° C. (the star marks denote the onset-point for the saturated reactivity); (C) hydrolysis profiles of MPO by UiO-66S with the different temperature at 99% RH (the star marks denote the onset-point for the saturated reactivity); and (D) the $\ln(C_t/C_0)$ vs. t plot for hydrolysis of MPO under controlled conditions.

$^a$The catalytic reaction methods are illustrated in FIGS. 4B, 9C, and 13A.
$^b$The reaction rate constant was determined from $\ln(C_t/C_0)$ vs. t plots.
$^c$The TOF values were determined at 50% unless otherwise specified.
$^d$The TOF values were calculated using conversions at 10 min.
$^e$Although the general procedure for the reactions was similar to Method 3, the fresh UiO-66 powder was added to the reaction solution. However, the typical Method 3 uses the suspension of UiO-66 in methanol.
$^f$The molecular weight of LPEI is 2,500 g/mol.
Ref. 3: Moon, S. Y. et al., Instantaneous Hydrolysis of Nerve-Agent Simulants with a Six-Connected Zirconium-Based Metal-Organic Framework, Angew. Chem. Int. Ed., 2015, 54: 6795 to 6799.
Ref. 4: Katz, M. J. et al., Exploiting Parameter Space in MOFs: A 20-Fold Enhancement of Phosphate-Ester Hydrolysis with UiO-66-NH$_2$, Chem. Sci., 2015, 6: 2286 to 2291.
Ref. 5: Moon, S. Y. et al., Detoxification of Chemical Warfare Agents Using a Zr6-Based Metal-Organic Framework/Polymer Mixture, Chem., 2016, 22: 14864 to 14868.

Figure 6:
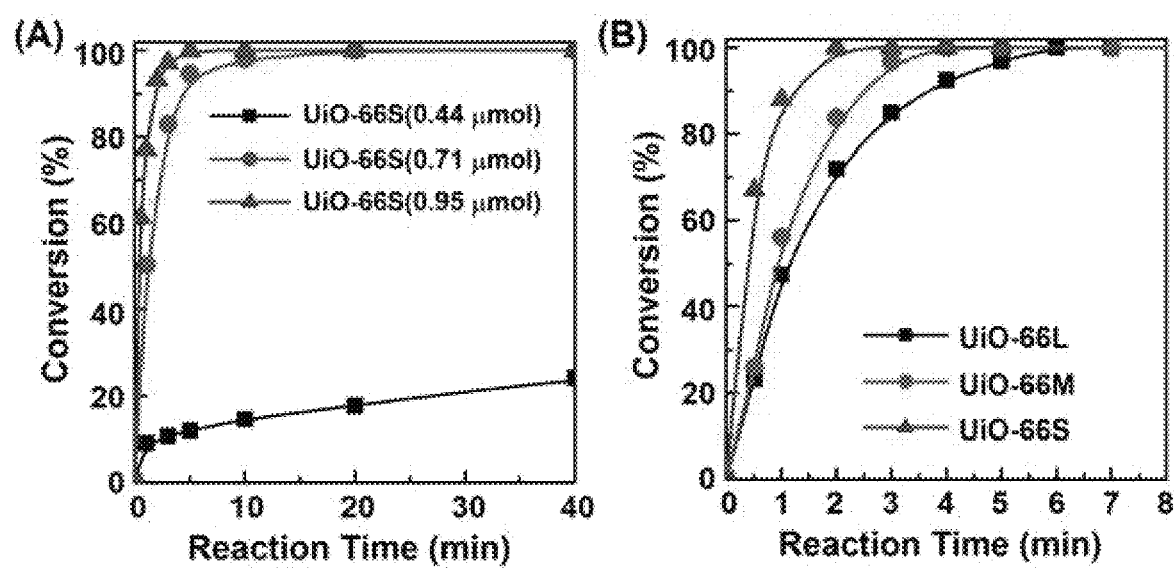
FIG. 6 shows (A) hydrolysis profiles of MPO in the presence of UiO-66S (0.98 μmol) by varying its loading mass and (B) hydrolysis profiles of MPO in the presence of UiO-66L, UiO-66M, and UiO-66S (0.98 μmol each) along with 4-EM.

To optimize the conditions for hydrolysis of MPO, the catalyst loading content of UiO-66S, which has an inverse proportional relationship with TOF (Equation 2), was reduced to 0.71 μmol and 0.44 μmol from 0.95 μmol, and the TOF values were substantially degraded to 0.235 sec$^{-1}$ and 0.014 sec$^{-1}$, respectively (FIG. 6A and Table 5, entries 3 to 5). When the UiO-66S loading content was increased to be greater than 0.95 μmol, the catalytic activity was mostly retained, resulting in the reduction in TOF. Therefore, 0.95 μmol was selected as the catalyst loading content for all reactions hereinafter. A half-life ($t_{1/2}$) value is also commonly used to determine the catalytic activity of catalysts, and in particular, for the applications in the MOF-based catalytic reactions for detoxification of chemical warfare agents (CWA). For a first-order reaction, $t_{1/2}$ may be determined by $t_{1/2}$=0.693/k. The $t_{1/2}$ value of UiO-66S was calculated to be 0.3 min and sequentially followed by UiO-66M (0.6 min) and UiO-66L (1.0 min) (FIG. 6). The underlying reason for the kinetically faster hydrolysis of MPO by UiO-66S, compared to those of UiO-66M and UiO-66L, may be because factors such as particle size, missing linker number effects, etc. are important parameters in catalytic reactions, and that UiO-66S has the smallest particle size (ca. 100 nm) and larger numbers of missing linkers (ca. 1.8) compared to those of UiO-66M and UiO-66M (Table 2). Comparing the catalytic activity of UiO-66S in the hydrolysis of MPO to those of known Zr(IV)-based MOFs including UiO-66, UiO-66-NH$_2$, and Nu-1000, it was found that the UiO-66S has superior catalytic activity, with respect to their TOF and $t_{1/2}$ values (Table 5, entries 3 and 12 to 14). These results suggest that the catalytic activity of UiO-66 for the hydrolysis of MPO can be controlled by a simple approach of varying the reaction concentration during the synthesis of UiO-66.

Figure 7:
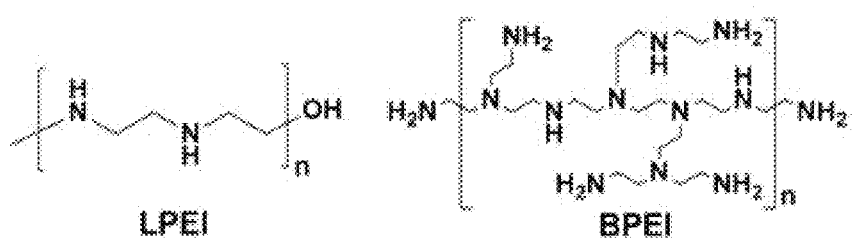
FIG. 7 shows (A) chemical structures of linear-type polyethyleneimine (LPEI) and branch-type polyethyleneimine (BPEI); the conversion plot for hydrolysis of MPO by UiO-66S (0.95 μmol) as a function of LPEI10k loading mass determined by a reaction for 20 mM; and (C) the $\ln(C_t/C_0)$ vs. t plot for hydrolysis of MPO by UiO-66S (0.95 μmol) in the presence of PEI bases (9 mg) including LPEI10k, BPEI10k, and BPEI0.6k.
Figure 7:
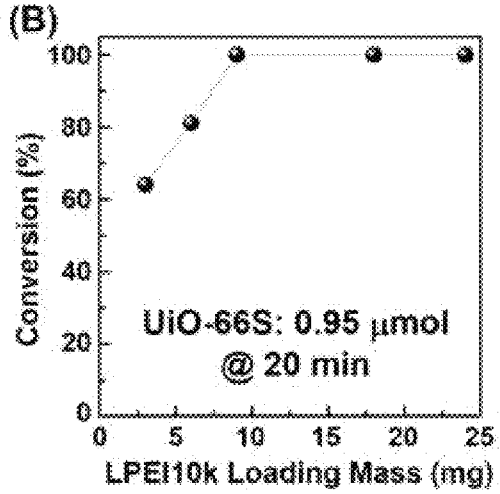
Figure 7:
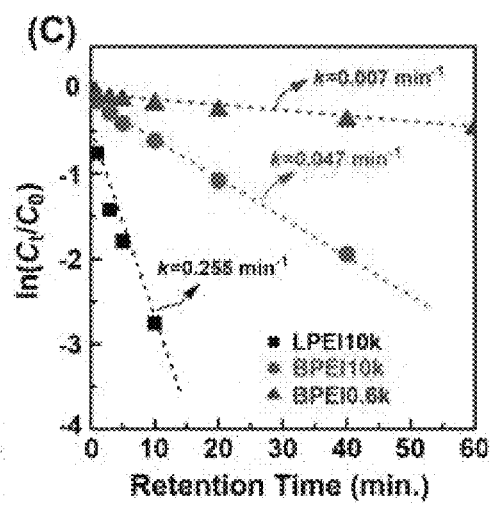
Figure 8:
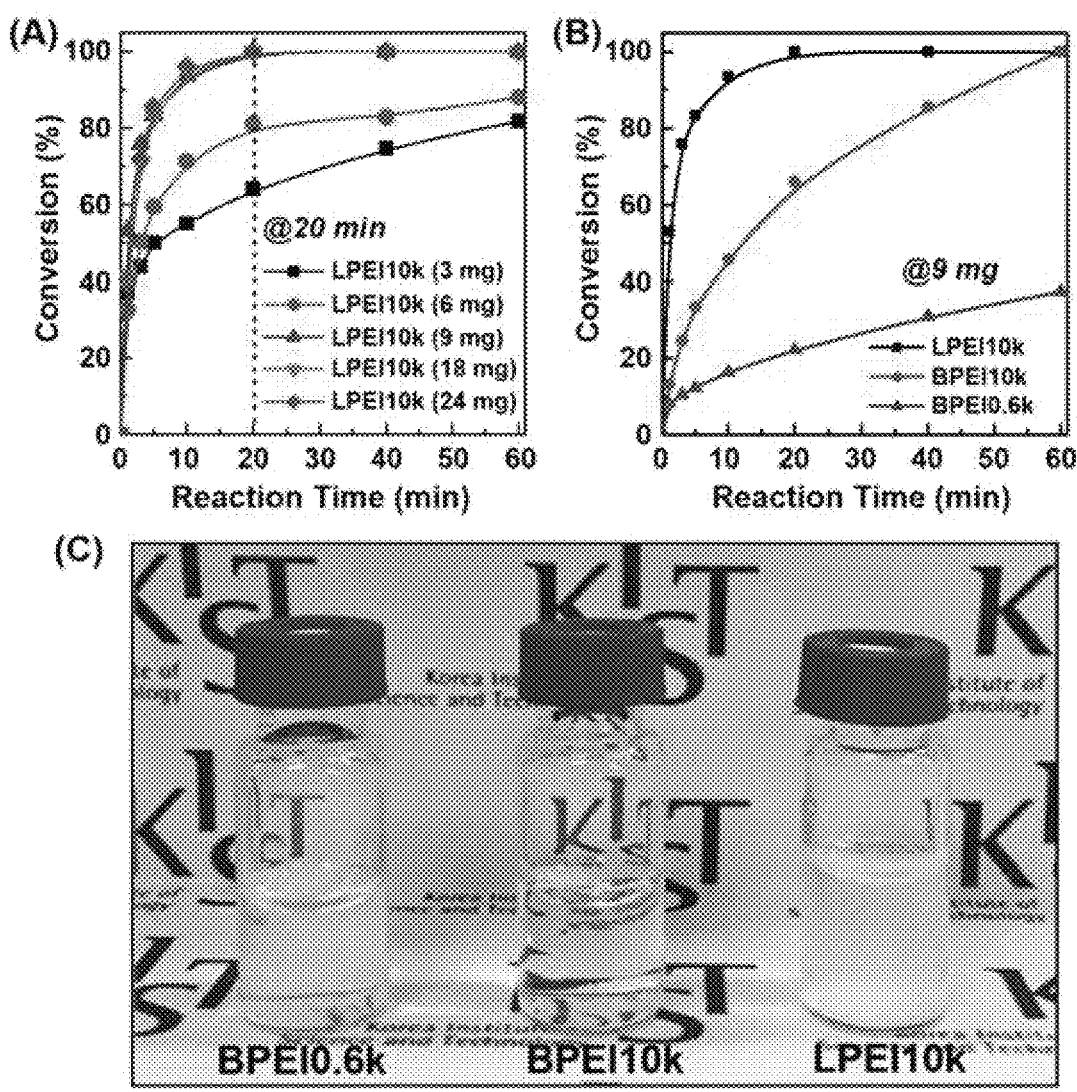
FIG. 8 shows (A) hydrolysis profiles of MPO in the presence of UiO-66S (0.95 μmol) with LPEI10k by varying its loading mass; (B) hydrolysis profiles of MPO in the presence of UiO-66S (0.98 μmol) in the presence of 9 mg of different PEIs; and (C) representative images for water solutions of BPEI0.6k, BPEI10k, and LPEI10k (9 mg/mL).

Recent studies with regard to catalytic activity of Zr(IV)-based MOFs in detoxification of CWAs suggested that all reactants must be in a solid state for the actual application such as protective suits and masks. For the enhanced feasibility with the MOF catalysts, the LPEI was previously proposed as a solid (a base material), which can replace the liquid type base of 4-EM. In addition, LPEI with a combination of UiO-66 and Nu-1000 allowed the catalytic activity as high as 4-EM to be achieved (ACS Catal., 2015, 5: 4637 to 4642; Chem. A Eur. J., 2016, 22: 14864 to 14868). The test results with regard to the high feasibility drew public attention to confirm the enhanced feasibility of Zr(IV)-based MOF catalysts for detoxification of CWAs. In this regard, the hydrolysis rate of UiO-66S with MPO was examined in the presence of either BPEI0.6k (MW: 600 g/mol), BPEI10k (MW: 10,000 g/mol), or LPEI10k (MW: 10,000 g/mol). The chemical structures of LPEI and BPEI are illustrated in FIG. 7A, and from these structures, it was confirmed that these compounds include sufficient amine sites which can act as a Brønsted base. First, the hydrolysis of MPO with various loading mass of LPEI10k as a controlled parameter was performed using Method 1 in the presence of UiO-66S (0.95 μmol) (FIGS. 7B and 8A). FIG. 7B shows the MPO hydrolysis conversion at 20 min according to the LPEI10k loading mass, in which the increase of LPEI10k loading mass from 3 mg to 9 mg allowed uphill conversions. However, a further increase of the LPEI10k loading mass exceeding 9 mg led to reaction saturation (FIG. 8A). Although the combination of UiO-66S and LPEI10k (9 mg) showed lower catalytic activity in the k (0.225 min$^{-1}$), TOF (0.219 sec$^{-1}$), and tin, (1.0 min) values compared to those of the UiO-66S and 4-EM combination (k=2.121 min$^{-1}$, TOF=0.548 sec$^{-1}$, and $t_{1/2}$=24 sec), the values indicated more enhanced catalytic activity relative to those of conventional catalysts with 4-EM or LPEI (2.5 k) (Table 5, entries 3, 6, and 12 to 15). These results may be due to the intrinsic features of UiO-66S, which involve a smaller particle size and more extensive active sites. In hydrolysis of MPO in the presence of UiO-66S, 9 mg of the PEI loading mass was selected as the optimized conditions in subsequent reactions with PEI.

The present inventors expected that BPEI, which had not been examined for MPO hydrolysis and is water-soluble, can induce higher catalytic activity than LPEI, which has lower water solubility. With the optimized PEI loading mass (9 mg), a hydrolysis reaction with MPO was performed in the presence of BPEI10k or BPEI0.6k, and as a result, the catalytic activity was shown to decrease in the following order: LPEI10k>>BPEI10k>BPEI0.6 k (FIGS. 7C and 8B and Table 5, entries 6 to 8). With regard to the comparison between LPEI10k and BPEI10k, the results obtained by the presence of PEIs cannot be explained by homogeneous and heterogeneous reactions. In addition, according to Moon's report, the relatively low molecular weight of LPEI can provide higher catalytic activity in the hydrolysis of MPO because of the varying pH (pH 9.2 (MW 2,500) and pH 7.7 (MW 250,000)) according to the molecular weight of LPEI, which is a highly important parameter to act as a Brønsted base (*Chem. A Eur. J.*, 2016, 22: 14864 to 14868). The present inventors considered that the alteration of pH according to the molecular weight of LPEI can be derived from the solubility differences in water because they fixed the introduced amine content (0.31 mmol) (FIG. 8C). However, although BPEI0.6k and BPEI10k have good water solubility and their pH values were mostly similar at ca. 11.0 and higher than that of LPEI10k (pH 9.0), BPEI10k showed higher catalytic activity than that of BPEI0.6k (FIGS. 7C and 8C). From these experimental results, it was predicted that good solubility of BPEI as a Lewis base can be easily chelated with the unsaturated Zr(IV) Lewis acid sites, which can act as active sites for hydrolysis of MPO based on the reported reaction mechanism.

Figure 9:
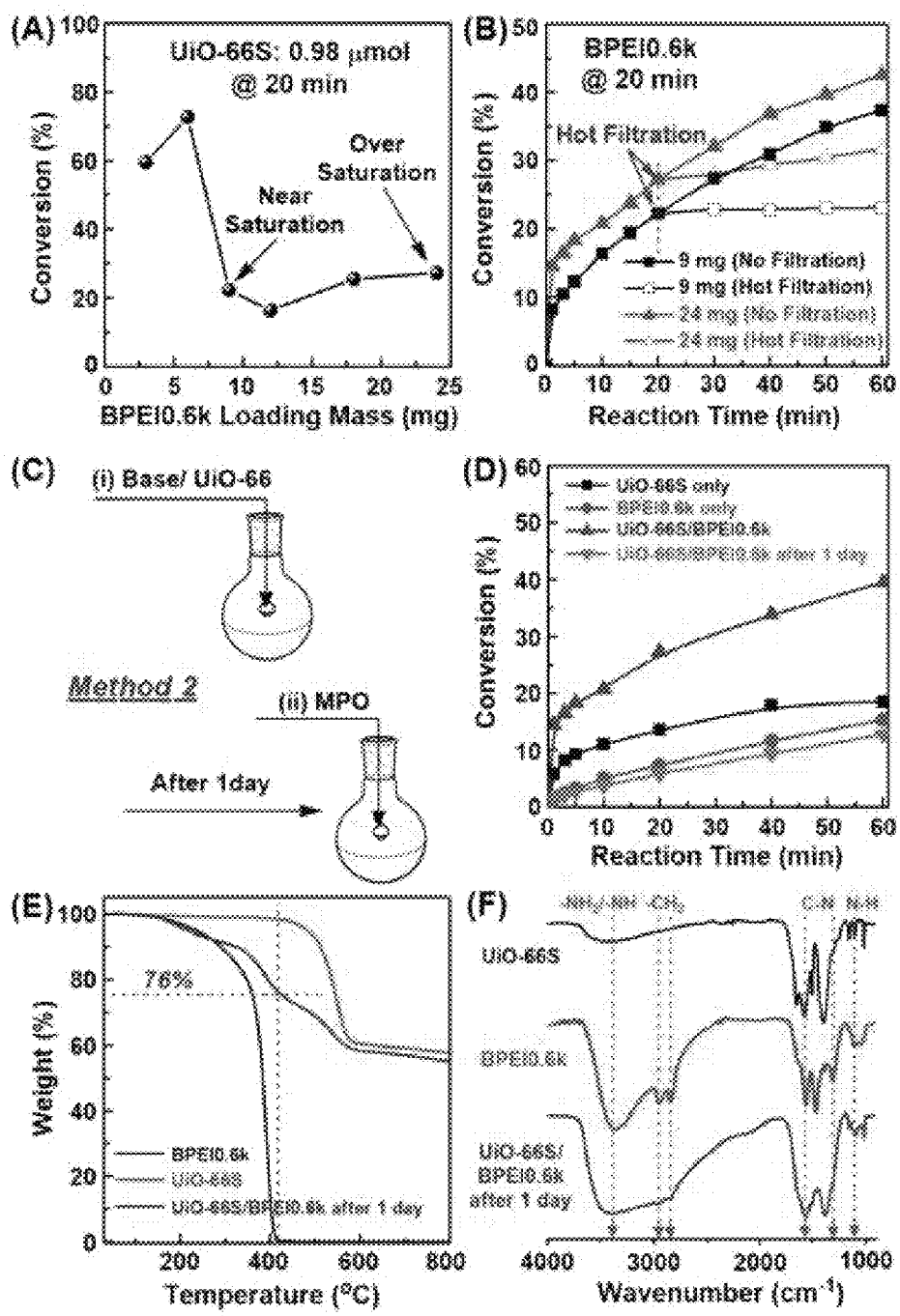
FIG. 9 shows (A) the conversion plot for hydrolysis of MPO by UiO-66S(0.95 mol) as a function of BPEI0.6k loading mass determined by a reaction for 20 mM; (B) hydrolysis profiles of MPO by UiO-66S (0.95 μmol) in the presence of 9 mg or 24 mg of BPEI0.6k, tested with and without hot filtration at 20 min; (C) a proposed catalytic reaction process of Method 2, in which (i) a base/UiO-66 mixture is prepared, and (ii) after 1 day, MPO is finally added to the mixture; (D) hydrolysis profiles of MPO by UiO-66S only (0.95 μmol), BPEI0.6k only (24 mg), and UiO-66S (0.95 μmol) with BPEI0.6k (24 mg) using Method 1, and UiO-66S (0.95 μmol) with BPEI0.6k (24 mg) using Method 2; (E) TGA curves of BPEI0.6k, UiO-66S, and the UiO-66S/BPEI0.6k mixture after 1 day (assignments by dotted lines are based on the BPEI structure and the peaks at 1593 cm$^{-1}$/1395 cm$^{-1}$ and 1510 cm$^{-1}$ corresponded to asymmetric/symmetric COO$^-$ stretching and a C=C benzene ring of UiO-66S, respectively); and (F) FT-IR spectra of BPEI0.6k, UiO-66S, and the UiO-66S/BPEI0.6k mixture after 1 day (assignments by dotted lines are based on the BPEI structure and the peaks at 1593 cm$^{-1}$/1395 cm$^{-1}$ and 1510 cm$^{-1}$ corresponded to asymmetric/symmetric COO$^-$ stretching and a C=C benzene ring of UiO-66S, respectively).
Figure 10:
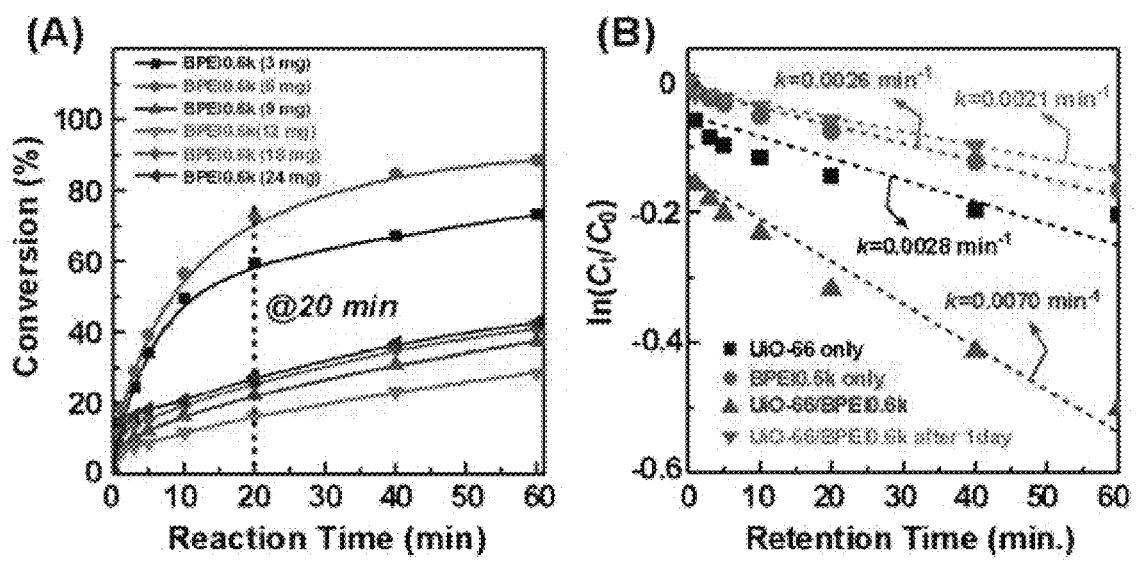
FIG. 10 shows (A) hydrolysis profiles of MPO by UiO-66S (0.98 μmol with BPEI0.6k by varying its loading mass; and (B) the $\ln(C_t/C_0)$ vs. t plot for hydrolyses of MPO by UiO-66S only (0.98 μmol), BPEI0.6k only (24 mg), and UiO-66S (0.98 μmol) with BPEI0.6k (24 mg) using Method 1, and UiO-66S (0.98 μmol) with BPEI0.6k (24 mg) using Method 2.

To verify the hypothesis with regard to the chelation of the active sites on UiO-66, a hydrolysis reaction with MPO was performed according to the loading mass of BPEI0.6k (FIGS. 9 and 10). FIG. 9 shows the conversion points of MPO hydrolysis as a function of the BPEI0.6k loading mass, and these points were obtained at 20 min in the coversion vs. time plots in FIG. 10. The conversion point at 6 mg loading of BPEI0.6k showed the highest conversion (72.7%), and then the conversion was drastically decreased to 16.3% at the 12 mg loading mass. A further increase in the loading mass of the BPEI0.6k up to 24 mg led to a slight increase in the conversion (27.3%). From these results obtained by varying the BPEI0.6k loading mass, it was found that the trend of the conversion plot can be associated with a decrease of active sites by the reactions between a BPEI Lewis base and UiO-66S Lewis acid sites. Further, the slight enhancement of the conversion with an increase of the BPEI0.6k loading mass from 12 mg may be ascribed to the hydrolysis reaction by free BPEI0.6 after over-saturation for the active sites of UiO-66S.

To confirm the hypothesis of the catalytic reaction by free BPEI, a hot-filtration method, which is used in heterogeneous catalytic reactions, was used. Two conversion points (e.g., 9 mg for the near-saturation point and 24 mg for the over-saturation point) were selected in FIG. 9A. The hydrolysis reactions were performed with the different BPEI0.6k loading mass (9 mg and 24 mg), and the conversions were monitored by $^{31}$P NMR (FIG. 9B). After the reaction began, the reaction solutions were filtered at 20 min to remove the UiO-66S. Then, interesting results were observed in the change of the conversion according to the reaction time (FIG. 9B). The near-saturation condition (9 mg) resulted in good retention in the reaction conversion after hot-filtration. In contrast, the over-saturation condition (24 mg) exhibited increased the conversion even after the hot-filtration (FIG. 9B). These results suggest that the catalytic activity of UiO-66S can be inhibited by the presence of BPEI because of the presence of BPEI on the UiO-66S as well as BPEI can act as a catalyst for the hydrolysis of MPO.

Despite the indirect discovery that the PEI can react with UiO-66S by an acid-base reaction, more explicit results are still required to verify the reduced catalytic activity by the active site chelation phenomenon. In addition, considering from the aspects of the long-term storage and the ready-to-use state for actual applications of real-time detoxification of CWAs, stable reactivity of Zr(IV)-based MOF catalysts is very important. Therefore, a reaction for the hydrolysis of MPO was performed according to a new method (Method 2). Specifically, the MPO solution was added to the prepared BPEI and UiO-66 aqueous solution after one day, as illustrated in FIG. 9C. This approach indicates that the retention time is provided with regard to the reaction between BPEI0.6k and UiO-66S. The catalytic activity for UiO-66S only and that for BPEI0.6k only were measured by using UiO-66S/BPEI0.6k with Method 1 and by using UiO-66S/BPEI0.6k with Method 2, respectively (FIG. 9D). The hydrolysis of MPO by UiO-66S only and by BPEI0.6k only resulted in an increase of the reaction conversion with the increase of the retention time. This catalytic behavior coincided with the increase of conversion in the hot-filtration reactions (24 mg) (FIG. 9B). The results by a UiO-66S/BPEI0.6k mixture with Method 2 showed a substantial decrease in catalytic activity (k=0.0021 min$^{-1}$) compared to the results obtained by a UiO-66S/BPEI0.6k mixture with Method 1 (k=0.0070 min$^{-1}$), even lower than that of BPEI0.6k only (k=0.0026 min$^{-1}$) (FIGS. 9D and 10B). These comparison results also strongly indicated that BPEI0.6k can react with UiO-66S and thereby prevent the hydrolysis reaction with MPO by passivation of the UiO-66S surface.

To confirm the BPEI0.6k content introduced onto UiO-66S, TGAs were measured for BPEI0.6k and UiO-66S samples, and after one day for the UiO-66S/BPEI0.6k mixture sample (Method 2). To obtain the UiO-66S/BPEI0.6k sample after one day, the precipitates were obtained from the reaction solution of Method 2 by filtration, and subjected to rinsing and sonication with methanol several times to remove the free BPEI0.6k. The BPEI0.6k content introduced onto UiO-66S was calculated to be 24 wt % by the weight difference of the UiO-66S/BPEI0.6k at 416° C., which is a critical point for 100% thermal degradation of BPEI0.6k, and almost 100% retention of UiO-66S (FIG. 9E, indicated by blue dotted lines). The FT-IR spectrum of the UiO-66S/BPEI0.6k sample after one day revealed that BPEI0.6k was apparently introduced onto the UiO-66S by showing representative peaks of BPEI at 3,377 cm$^{-1}$, 2,955 cm$^{-1}$/2,836 cm$^{-1}$, 1,564 cm$^{-1}$/1,312 cm$^{-1}$, 1,470 cm$^{-1}$, and 1,115 cm$^{-1}$/1,049 cm$^{-1}$, which corresponded to —NH$_2$/—NH bending, asymmetric/symmetric —CH$_2$ stretching, C—N stretching, and N—H wagging of BPEI, respectively. As such, it was suggested that, with regard to the effects of using BPEI in the hydrolysis of MPO catalyzed by UiO-66, the BPEI activity may deteriorate during long-term retention of the UiO-66S/BPEI mixture and thus the actual use of BPEI in catalytic reactions may not be feasible.

Figure 11:
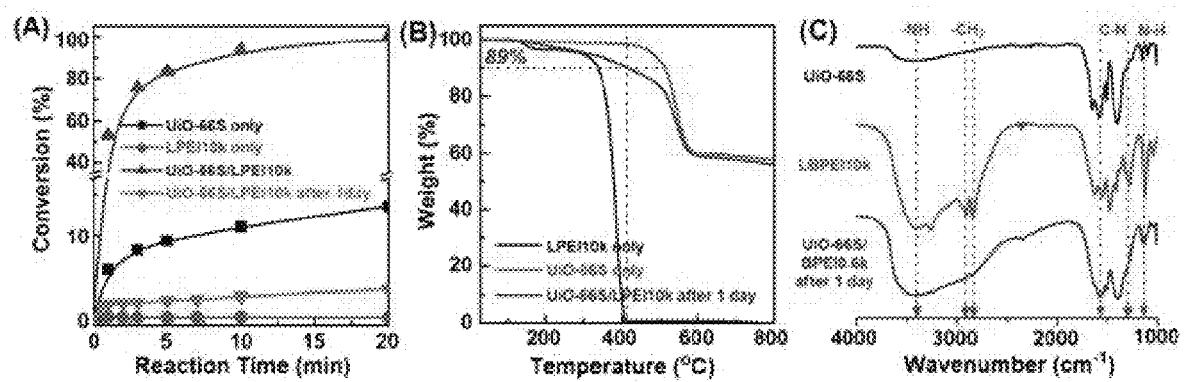
FIG. 11 shows (A) hydrolysis profiles of MPO by UiO-66S only (0.95 mol), LPEI10k only (9 mg), and UiO-66S (0.95 μmol) with LPEI10k (9 mg) using Method 1, and UiO-66S (0.95 μmol) with LPEI0.6k (9 mg) using Method 2; and (B) TGA curves of BPEI0.6k, UiO-66S, and the UiO-66S/BPEI0.6k mixture after 1 day (assignments by dotted lines are based on the LPEI structure and the peaks at 1593 cm$^{-1}$/1395 cm$^{-1}$ and 1510 cm$^{-1}$ corresponded to asymmetric/symmetric COO$^-$ stretching and a C=C benzene ring of UiO-66S, respectively); and (F) FT-IR spectra of BPEI0.6k, UiO-66S, and the UiO-66S/BPEI0.6k mixture after 1 day (assignments by dotted lines are based on the BPEI structure and the peaks at 1593 cm$^{-1}$/1395 cm$^{-1}$ and 1510 cm$^{-1}$ corresponded to asymmetric/symmetric COO$^-$ stretching and a C=C benzene ring of UiO-66S, respectively).
Figure 12:
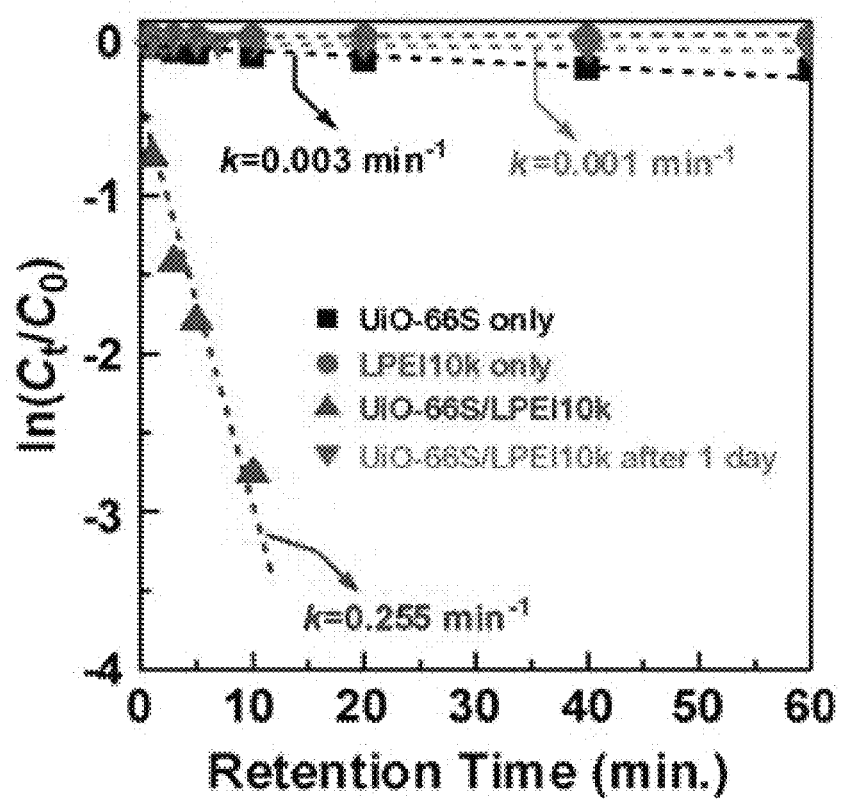
FIG. 12 shows the results of the $\ln(C_t/C_0)$ vs. t plot for hydrolysis of MPO by UiO-66S only (0.95 mol), LPEI10k only (9 mg), and UiO-66S (0.95 μmol) with LPEI10k (9 mg) using Method 1, and UiO-66S (0.95 μmol) with LPEI0.6k (9 mg) using Method 2.

Based on the experiments with BPEI, it should be considered that the deterioration of catalytic activity of BPEI cannot be avoided after the long-term retention of the UiO-66/LPEI mixture in a mixture state. To confirm the long-term stability of the catalytic activity, Method 2 with UiO-66S and LPEI10k was applied for the hydrolysis reaction of MPO. FIG. 11 shows that LPEI10k does not have a catalytic property for the hydrolysis of MPO. One-day retention of the UiO-66S/LPEI10k mixture resulted in substantial deterioration in the catalytic activity (TOF=0.001 sec$^{-1}$) relative to that obtained by Method 1 (TOF=0.219 sec$^{-1}$) (FIG. 11A and Table 5, entries 6 and 9). In addition, the rate constant value obtained by Method 2 showed a 255-fold decrease compared to the value obtained by Method 1 (FIG. 12).

The quantity of LPEI10k introduced onto UiO-66S was determined using TGA. The TGA sample was prepared by washing and sonication of precipitates with an excess of methanol after the Method 2 reaction with UiO-66S and LPEI10k. The TGA curves revealed that 11 wt % of LPEI10k remained on UiO-66S, which was calculated by weight change of the UiO-66S/LPEI10k sample after one day at 416° C. (FIG. 11B). In addition, the FT-IR spectrum of the UiO-66S/LPEI10k sample after one day confirmed the presence of LPEI10k onto UiO-66S by showing representative peaks of LPEI at 3,430 cm$^{-1}$, 2,915 cm$^{-1}$/2,846 cm$^{-1}$, 1,572 cm$^{-1}$/1,317 cm$^{-1}$, 1,470 cm$^{-1}$, and 1,156 cm$^{-1}$/1,133 cm$^{-1}$, which corresponded to —NH bending, asymmetric/symmetric —CH$_2$ stretching, C—N stretching, and N—H wagging of LPEI, respectively. These experimental results obtained using the UiO-66 composite with LPEI suggested that the LPEI candidate as an alternative for 4-EM will be difficult to apply in the real-time detoxification of CWAs.

A solid-state system for catalytic hydrolysis of MPO using UiO-66S and LPEI10k can provide a specific example to address its feasibility in the applications in protective suits and masks. For this purpose, in the present invention, a cotton fabric was used as a support and the suspension of UiO-66S (1.1 mg)/LPEI10k (4.5 mg) in methanol (0.2 mL) was coated on the cotton fabric (FIG. 13(A1) and (A2)). The UiO-66S/LPEI10k composite coated cotton fabric was applied as a catalyst and tested for hydrolysis of MPO under controlled conditions for reflecting the actual events (FIG. 13(A3)). In particular, the two parameters of humidity and temperature were considered. Humidity is the most important factor for hydrolysis reactions because the reactions cannot occur without water. In addition, the temperature can provide the energy for overcoming the activation energy for a substitution reaction between H$_2$O and MPO in the ligation with Zr(IV) because the binding free energy for Zr-MPO is relatively high compared to that for interaction between UiO-66 and MPO.

The control of humidity as a reaction parameter suggested that the hydrolysis of MPO is the humidity-dependent reaction showing a substantial conversion difference in the initial reaction step (FIG. 13B). Moreover, the reaction conversions were saturated during the reaction. This result was thought to be due to a decrease of reactive sites on UiO-66S by chelating with LPEI10k in the presence of high humidity. This was indirectly confirmed by observing a shift of the onset-point to the higher reaction time from 5 hours (at 99% RH) to 13 hours (at 65% RH). The plots for hydrolysis of MPO according to the temperature changes from 15° C. to 40° C. suggested that a temperature parameter is less effective for the hydrolysis reaction than that by humidity changes even though the increasing temperature allowed an increase of the hydrolysis rate (FIG. 13C). In addition, the change of the onset-points according to the temperature did not show any substantial difference relative to the change by humidity (FIGS. 13B and 13C). For comparative evaluation, the ln($C_t/C_0$) vs. t plots were used, and the substantially saturated point (at 24 hours) in the conversion changes was ignored for reasonable calculation of k by pseudo-first-order reaction kinetics (Equation 1). The resulting k values according to different conditions of temperature and humidity suggested that the condition at 40° C. and 99% RH is the optimized conditions for the hydrolysis of MPO. The k value (0.078 h$^{-1}$) at the optimized condition was about 200 times lower than the value (15.3 h$^{-1}$) obtained by the solution sate system (Table 5, entry 6). In contrast, the result by Method 2 (k=0.06 h$^{-1}$) was mostly consistent with the result under the optimized conditions (k=0.078 h$^{-1}$) even though Method 2 was performed in the aqueous solution system (Table 5, entry 9). This indicates that the approach for the UiO66S/LPEI10k composite coating system has low feasibility, as well as that the catalytic activity in the combination of UiO-66S and LPEI10k is highly dependent on the reaction process. In addition, the LPEI10k coated UiO-66S did not exhibit excellent catalytic activity for the hydrolysis of MPO regardless of the state of the reaction conditions, except the case by Method 1 where a base and the catalyst are mixed immediately before the hydrolysis reaction.

Figure 14:
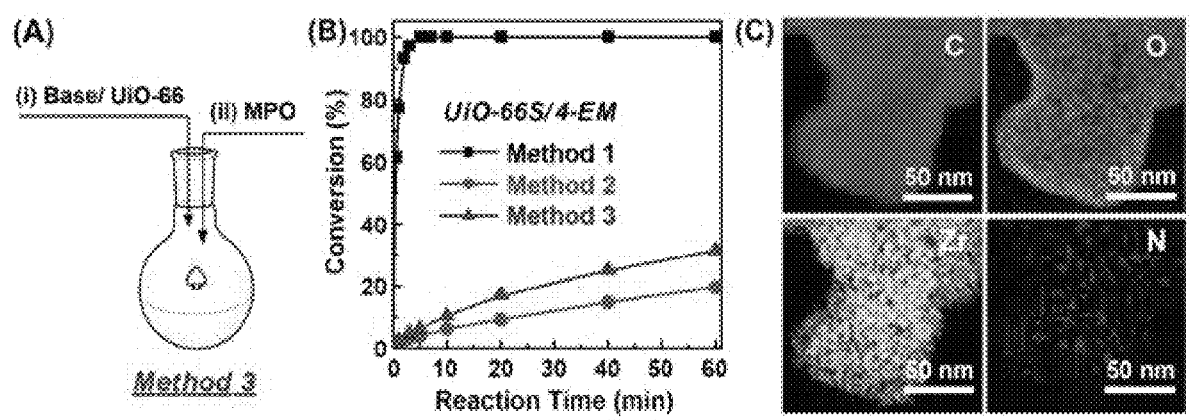
FIG. 14 shows (A) a catalytic reaction process of Method 3, in which (i) a base/UiO-66 mixture is prepared, and (ii) UiO-66 is added to the mixture; (B) results of comparison of hydrolysis profiles of MPO by a combination of UiO-66S (0.95 μmol) and 4-EM (450 mM) with different reactions by Method 1 and Method 2; and (C) results of element mapping of STEM-EELS of UiO-66S after the hydrolysis using UiO-66S and 4-EM by Method 2 (see FIGS. 4B and 9C).
Figure 15:
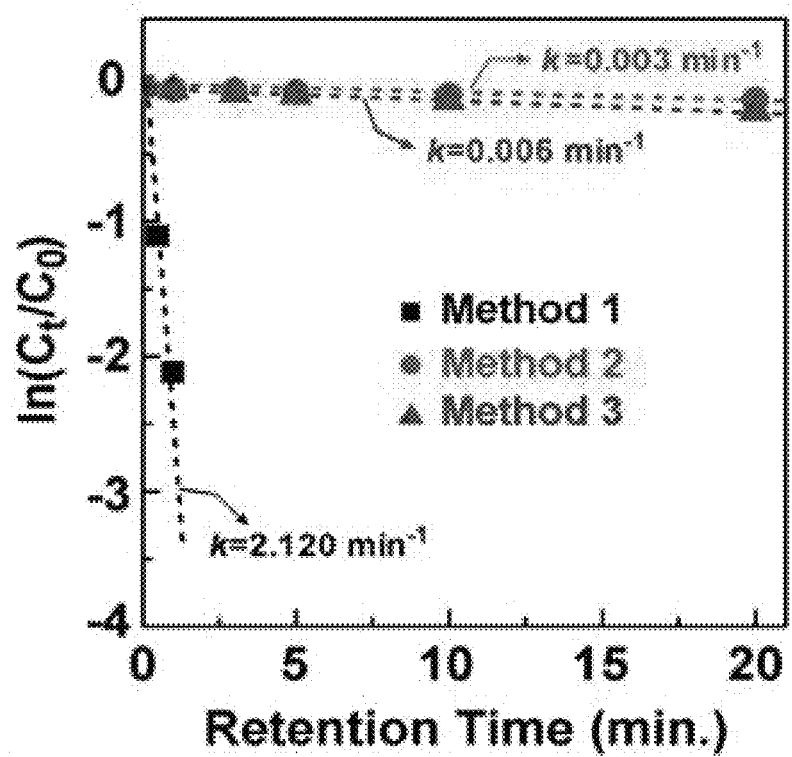
FIG. 15 shows the results of the $\ln(C_t/C_0)$ vs. t plot for hydrolysis of MPO by Method 1 to Method 3 in the presence of UiO-66S only (0.95 μmol) and 4-EM (450 mM) (see FIGS. 4B, 9C, and 14A).

From the feasibility tests with PEIs, it was examined whether or not the presence of 4-EM in the Method 2 reaction can maintain the intrinsic catalytic activity of UiO-66S. In addition, it was examined when 4-EM react with Lewis acid sites on UiO-66S due to a high pH value of 4-EM (10.9), how the reaction rate is accelerated. To confirm these two issues, Method 3 was performed, in which the MPO solution was added to the prepared suspension containing UiO-66S and 4-EM in one minute, as illustrated in FIG. 14A. With a combination of UiO-66S and 4-EM, the hydrolysis of MPO was performed using the three different methods suggested in the present invention (FIG. 14B). The results by Method 2 and Method 3 revealed that 4-EM immediately affects the catalytic activity of UiO-66S based on the observations that similar k values (0.003 min$^{-1}$ and 0.006 min$^{-1}$, respectively) and TOF values (0.003 sec$^{-1}$ and 0.005 sec$^{-1}$, respectively) regardless of the retention time after preparation of the UiO-66S and 4-EM mixture (FIG. 15 and Table 5, entries 10 and 11). These values by Method 2 and Method 3 exhibited a significant decrease of the catalytic activity compared to the results by Method 1, and the TOF values were decreased by about 200- and 100-fold, respectively (Table 5, entries 3, 10 and 11). To confirm the introduction of 4-EM into UiO-66S by Method 2 and Method 3 as shown in the case of PEI/UiO-66, TGA and FT-IR analyses were performed. However, the low quantity introduction and small molecular weight of 4-EM rendered their characterization difficult. As such, further analysis was performed using the STEM-EELS element mapping method that can identify the elements contained in a small amount in particles, and the results are shown in FIG. 14(D). As shown in FIG. 14(D), it was confirmed that the N group, which is absent in the chemical structure of UiO-66S itself, was uniformly found in UiO-66S particles after the hydrolysis reaction in the presence of a base, and this result confirms that 4-EM, which is the only reactant that has the N group among the reactants, is introduced to UiO-66S. As such, it will still be challenging for the use of 4-EM as a base material with UiO-66 catalysts for composite materials to have good feasibility because of the suggested acid-base reaction resulting in significantly reduced catalytic activity after its long-term storage.

Figure 16:
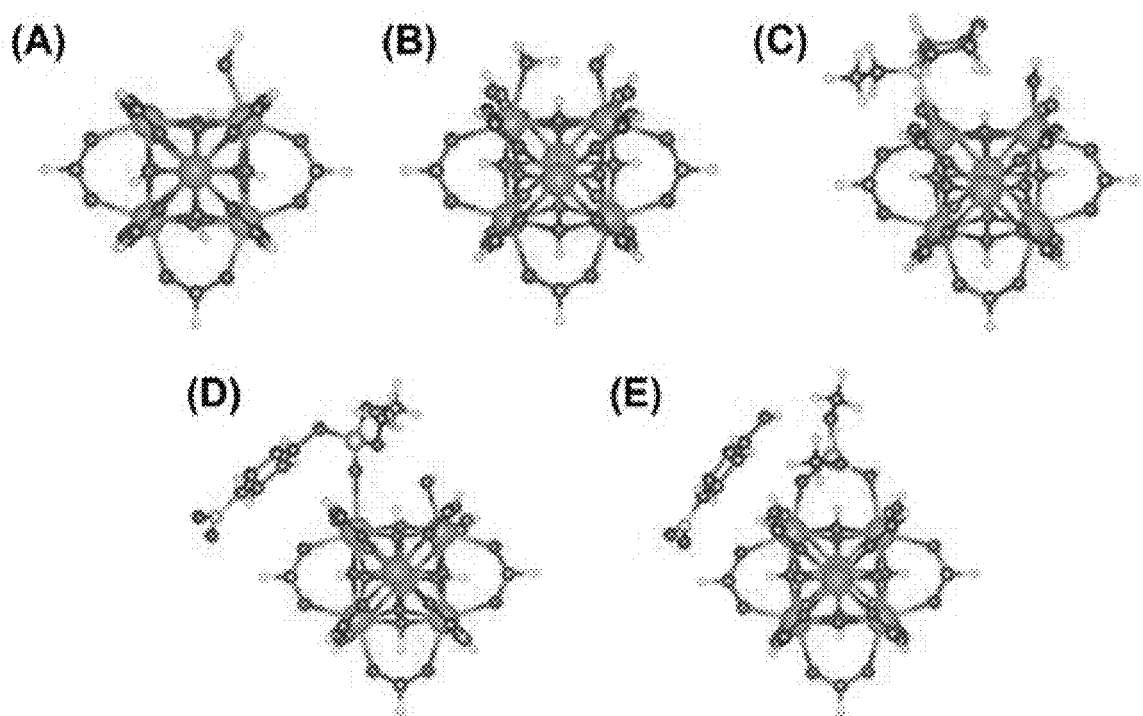
FIG. 16 shows the geometries used in the calculation according to the present invention, in which (A) to (E) represent UiO66_OH, UiO66_H$_2$O, UiO66_4-EM, UiO66_MPO, and UiO66_MPO_H$_2$O, respectively (color codes of the atoms are Zr=green, O=red, H=white, C=brown, P=dark pink, and N=light purple).
Figure 17:
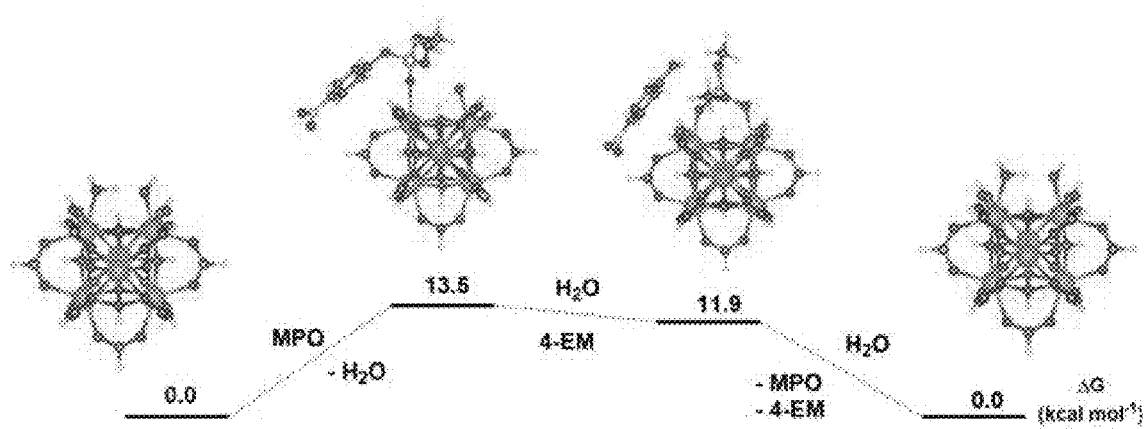
FIG. 17 shows reaction energies calculated by density functional theory (DFT) for 4-EM binding on UiO-66 and the substitution of 4-EM with MPO (color codes of the atoms are Zr=green, O=red, H=white, C=brown, P=dark pink, and N=light purple).

For further understanding of the substantial reduction in catalytic activity of the MPO hydrolysis performed by Method 2, quantum chemical calculations were carried out at the density functional theory (DFT) calculation level. FIG. 16 shows all of the geometries of the MOF-agent complexes optimized in the present DFT calculations, and free energy changes for the relevant reactions are presented in Table 6. The substitution reaction free energy of MPO by 4-EM on UiO-66 (the 6$^{th}$ reaction in Table 6) was slightly increased (7.5 kcal mol$^{-1}$), which indicates that the reaction would not easily occur under the atmosphere environment. The simulation result can support the experimental results that Method 2 and Method 3 show low reaction rates. When 4-EM passivates the defect sites in UiO-66, it is difficult for the MPO substitution reaction to occur for the post catalysis. Therefore, an attempt was made to examine why Method 1 shows a fast reaction rate even though MPO has a lower binding energy (16 kcal mol$^{-1}$) in UiO-66 compared to H$_2$O (29.5 kcal/mol). Although the binding free energy is greater for H$_2$O molecules, the environment is water itself, and thus the substitution of the attached H$_2$O molecules was allowed to occur frequently. Energetically, the substitution activation of MPO by H$_2$O may be more difficult than that of the reverse situation, but the explicit values were not possible in this work due to the excessive calculation work required. After the formation of a chemical bond between MPO and UiO-66, the activation of this relatively large molecule to be detached may not be so easy when compared to the detachment of H$_2$O molecules. It was found that the catalysis of MPO on UiO-66 occurs on one Zr metal atom defect site in the last row of Table 6. However, as shown in FIG. 16E, the stable geometry of MPO+H$_2$O on UiO66 has a bond between P on MPO and OH groups on another conjugate defect site on UiO66. Therefore, it was confirmed that the hydroxyl group on the other Zr site has an important role in the detoxification reaction process contrary to the previous mechanisms. The proposed new reaction mechanism is illustrated in FIG. 17.

TABLE 6

| Reaction | ΔG (kcal/mol) |
|---|---|
| UiO-66_OH + H$_2$O → UiO-66_H$_2$O | −29.5 |
| UiO-66_OH + MPO → UiO-66_MPO | −16.0 |
| UiO-66_OH + 4-EM → UiO-66_4-EM | −23.5 |
| UiO-66_H$_2$O + MPO → UiO-66_MPO + H$_2$O | 13.5 |
| UiO-66_H$_2$O + 4-EM → UiO-66_4-EM + H$_2$O | 6.0 |
| UiO-66_4-EM + MPO → UiO-66_MPO + 4-EM | 7.5 |
| UiO-66_MPO + H$_2$O + 4-EM → UiO-66_MPO_H$_2$O + 4-EM | −1.6 |

The various experimental methods and the reaction energy prediction by DFT described above have shown that long-term storage of MPO and bases including 4-EM and PEI can result in a substantial decrease of catalytic activity in the hydrolysis of MPO. To solve the problem, the development of new base materials to provide highly stable catalytic activity to Zr-based MOF catalysts as well as studies on new catalytic reaction processes (e.g., separate storage of catalysts and bases, and provision of fast mixing when exposed CWAs, etc.) remain as essential challenges for the suggested potential applications.

<Conclusion>

For high-performance catalysis, the modulated UiO-66 catalysts with three different defect densities and particle sizes were successfully synthesized by adjusting the hydrolysis of ZrCl$_4$ and deprotonation of BDC as a function of the solvent volume in the framework reactions. The use of a lower solvent volume resulted in the most active UiO-66 catalyst (UiO-66S) with the smallest UiO-66 particle size (ca. 100 nm) and the highest defect density (1.8 per cluster) which are favorable by Lewis acid-catalyzed reactions. The UiO-66S showed the substantially enhanced hydrolysis rate for MPO in the presence of the 4-EM base (TOF: 0.547 s$^{-1}$) compared to that of UiO-66L (low defect density: 1.6 per cluster, 1.88 s$^{-1}$). With UiO-66S, its feasibility in the presence of a polymeric base including LPEI and BPEI was examined. However, it was found that the catalytic performance was extremely dependent on the content of PEI in the MPO hydrolysis reactions because of the strong and fast ligation between Lewis acid Zr sites in UiO-66 and Lewis base amine sites in PEIs. Further, the one-day storage of UiO-66 and LPEI in a solution resulted in a 220-fold decrease in catalytic MPO hydrolysis rate compared to the result using a fresh mixture of UiO-66 and LPEI (from 0.001 s$^{-1}$ to 0.219 s$^{-1}$), and this is because the interaction between UiO-66 and PEI substantially reduced the Lewis acidic Zr active sites on UiO-66 based on the MPO hydrolysis mechanism. Based on the study results with regard to PEIs, the present inventors have found that 4-EM also affects the reactivity of UiO-66, which can also be explained by the acid-base interaction. To confirm the reactivity changes by chelation of organic bases, quantum chemical calculations at the density functional theories (DFT) calculation level were performed. The substitution reaction of 4-EM with MPO at the Zr sites in UiO-66 is an endergonic reaction (7.5 kcal mol$^{-1}$), which was supported by the fact that the reaction is difficult under ambient conditions. The extensive experimental and computational studies of the present invention suggested that development of rationally designed new base materials to incorporate with Zr(IV)-based MOF catalysts are still challenging, and additionally, substantial attention in studies for the reasonable catalytic reaction processes should be considered to provide stable and uniform catalytic reactions that employ Zr(IV)-based MOF catalysts incorporating Lewis base sites-contained materials.

The invention claimed is:

1. A method for preparing catalyst particles of UiO-66, comprising:
   providing a first solution comprising ZrCl$_4$ at a concentration of 0.15 M to 0.5 M, and a second solution comprising terephthalic acid (benzene-1,4-dicarboxylic acid; BDC) at a concentration of 0.1 M to 0.5 M; and
   mixing the first solution and the second solution in a volume ratio of 1:1 to 1:3,
   wherein the first solution comprises hydrochloric acid in an amount of 8 to 15 moles per mole of ZrCl$_4$, and
   the catalyst particles of UiO-66 have an average diameter of 50 nm to 400 nm, and hydrolyze or detoxify chemical warfare agents.

2. The method of claim 1, wherein both the first solution and the second solution are prepared using N,N-dimethylformamide (DMF) as a solvent.

3. The method of claim 1, wherein the third step is performed at 60° C. to 120° C. for 12 to 48 hours.

4. The method of claim 1, wherein the catalyst particles of UiO-66 have an average diameter of 100 nm to 190 nm.

5. The method of claim 1, wherein particles of the UiO-66 have 1.65 to 1.9 missing linker sites on average within a single cluster.

6. The method of claim 1, wherein particles of the UiO-66 have a specific surface area of 1400 m$^2$/g to 1500 m$^2$/g.

7. A method for detoxifying chemical warfare agents (CWA) with catalyst particles of UiO-66, the method comprising:
   providing a first solution comprising ZrCl$_4$ at a concentration of 0.15 M to 0.5 M, and a second solution comprising terephthalic acid (benzene-1,4-dicarboxylic acid; BDC) at a concentration of 0.1 M to 0.5 M; and
   mixing the first solution and the second solution in a volume ratio of 1:1 to 1:3,
   wherein the first solution comprises hydrochloric acid in an amount of 8 to 15 moles per mole of ZrCl$_4$ for making of the catalyst particles of UiO-66 having an average diameter of 50 nm to 400 nm;
   preparing a solution comprising a base and a chemical warfare agent in a water solvent; and contacting the solution comprising the base and the chemical warfare agent with the catalyst particles of UiO-66, wherein the method of detoxifying has a conversion rate of at least 50% at one minute or less of contact time as measured with a simulated warfare agent, methylparaoxone.

8. The method of claim 7, wherein the contacting of the solution and the catalyst particles includes a mole ratio of the catalyst particles of UiO-66 to chemical warfare agent of 0.02:1 to 0.05:1.

9. The use of the UiO-66 particles prepared by the method of claim 7, forming a coating for a fabric including the UiO-66 particles.

10. The use of the UiO-66 particles prepared by the method of claim 7, forming a molded product including the UiO-66 particles housed in a porous container product of a canister.

11. The use of the UiO-66 particles prepared by the method of claim 7, forming a molded product including the UiO-66 particles housed in a porous container of a canister for a protective mask.

\* \* \* \* \*